(12) United States Patent
Cope

(10) Patent No.: US 8,343,222 B2
(45) Date of Patent: Jan. 1, 2013

(54) SPINAL DISC PROSTHESIS AND INSTRUMENTS

(76) Inventor: Aiden Cope, Manchester (GB)

(*) Notice: Subject to any disclaimer, the term of this patent is extended or adjusted under 35 U.S.C. 154(b) by 808 days.

(21) Appl. No.: 11/912,582

(22) PCT Filed: Apr. 28, 2006

(86) PCT No.: PCT/GB2006/001583
§ 371 (c)(1),
(2), (4) Date: May 21, 2008

(87) PCT Pub. No.: WO2006/114646
PCT Pub. Date: Nov. 2, 2006

(65) Prior Publication Data
US 2010/0030336 A1 Feb. 4, 2010

(30) Foreign Application Priority Data

Apr. 28, 2005 (GB) .................................. 0508678.0
Nov. 8, 2005 (GB) .................................. 0522786.3

(51) Int. Cl.
*A61F 2/44* (2006.01)
(52) U.S. Cl. .................. 623/17.14; 623/17.15
(58) Field of Classification Search ..... 623/17.11–17.16
See application file for complete search history.

(56) References Cited

U.S. PATENT DOCUMENTS

| 5,314,477 | A |   | 5/1994  | Marnay       |          |
|-----------|---|---|---------|--------------|----------|
| 5,556,431 | A |   | 9/1996  | Buttner-Janz |          |
| 5,702,450 | A | * | 12/1997 | Bisserie     | 623/17.16 |
| 5,888,226 | A |   | 3/1999  | Rogozinski   |          |
| 6,113,637 | A |   | 9/2000  | Gill et al.  |          |
| 6,179,874 | B1|   | 1/2001  | Cauthen      |          |
| 6,692,495 | B1|   | 2/2004  | Zacouto      |          |
| 6,706,068 | B2|   | 3/2004  | Ferree       |          |

(Continued)

FOREIGN PATENT DOCUMENTS

EP      1374808     1/2004

(Continued)

OTHER PUBLICATIONS

Berry et al., "A Morphometric Study of Human Lumbar and Selected Thoracic Vertebrae," Spine, 1987, pp. 362-367, 12(4).

(Continued)

*Primary Examiner* — Andrew Yang
(74) *Attorney, Agent, or Firm* — Thompson Coburn LLP

(57) ABSTRACT

Described is an articulating intervertebral disc prosthesis including a first member having a vertebra engaging portion and a bearing surface; a second member having a vertebra engaging portion and a bearing surface, which in use abuts the first member bearing surface to form a first bearing joint, —and motion restraint means adapted to provide ax-ticulation restraint of the bearing joints at predetermined limits of articulation similar to the natural motion restraint of a facet joint; wherein the prosthesis is longitudinally—split into two bodies so that the two bodies can be laterally separated, each body having an articulating bearing joint. Preferably, the second member bearing surface is shaped to include at least a portion of a first substantially circular curve when viewed in a first section, and at least a portion of a second substantially circular curve when viewed in a second section, said first and second curves being of respectively different sizes of circle. Further described is a chisel and a chisel guide for preparing the disc space for implantation.

25 Claims, 27 Drawing Sheets

U.S. PATENT DOCUMENTS

| | | | |
|---|---|---|---|
| 6,770,095 B2 * | 8/2004 | Grinberg et al. | 623/17.14 |
| 7,083,649 B2 | 8/2006 | Zucherman et al. | |
| 2003/0074071 A1 | 4/2003 | Errico et al. | |
| 2004/0024462 A1 | 2/2004 | Ferree et al. | |
| 2004/0034426 A1 * | 2/2004 | Errico et al. | 623/17.13 |
| 2004/0073311 A1 | 4/2004 | Ferree | |
| 2004/0133281 A1 | 7/2004 | Khandkar et al. | |
| 2004/0153159 A1 | 8/2004 | Cauthen | |
| 2004/0176851 A1 | 9/2004 | Zubok et al. | |
| 2004/0181285 A1 | 9/2004 | Simonson | |
| 2004/0199253 A1 | 10/2004 | Link et al. | |
| 2004/0225364 A1 | 11/2004 | Richelsoph et al. | |
| 2004/0225365 A1 | 11/2004 | Eisermann et al. | |
| 2004/0243240 A1 | 12/2004 | Beaurain et al. | |
| 2005/0033435 A1 | 2/2005 | Belliard et al. | |
| 2005/0043800 A1 | 2/2005 | Paul et al. | |
| 2005/0154465 A1 | 7/2005 | Hodges et al. | |
| 2006/0259147 A1 * | 11/2006 | Krishna et al. | 623/17.15 |

FOREIGN PATENT DOCUMENTS

| | | |
|---|---|---|
| EP | 1647243 | 4/2006 |
| WO | 0024342 | 5/2000 |
| WO | 03059212 | 7/2003 |
| WO | 03065929 | 8/2003 |
| WO | 03090649 | 11/2003 |
| WO | 2004019830 | 3/2004 |
| WO | 2004064692 | 8/2004 |
| WO | 2004107952 | 12/2004 |
| WO | 2005011522 | 2/2005 |
| WO | 2005067824 | 7/2005 |

OTHER PUBLICATIONS

Gilad et al., "A Study of Vertebra and Disc Geometric Relations of the Human Cervical and Lumbar Spine," Spine, 1986, pp. 154-157, 11(2).
Pearcy et al., "Axial Rotation and Lateral Bending in the Normal Lumbar Spine Measured by Three-Dimensional Radiography," Spine, 1984, pp. 582-587, 9(6).
Pearcy et al., "Three-Dimensional X-ray Analysis of Normal Movement in the Lumbar Spine," Spine, 1984, pp. 294-297, 9(3).
Pearcy et al., "Instantaneous Axes of Rotation of the Lumbar Intervertebral Joints," Spine, 1988, pp. 1033-1041, 13(9).
Zhao et al., "Discogenic Origins of Spinal Instability," Spine, 2005, pp. 2621-2630, 30(23), Lippincott Williams & Wilkins.
Search Report for Corresponding GB0522786.3.
Communication under Rule 71(3) EPC for EP Application 06726963.9 dated Mar. 7, 2012.

* cited by examiner

SPINAL DISC PROSTHESIS AND INSTRUMENTS

The present invention relates to intervertebral motion segment prostheses, and to instruments for the accurate placement of intervertebral prostheses in the intervertebral space of a motion segment. In particular, the present invention relates to an intervertebral motion segment prosthesis having an articulating or bearing joint.

A spinal column (e.g. a human spinal column) is formed from a chain of vertebrae, and each vertebra can be divided into two portions, posterior and anterior.

The anterior portions of each adjacent vertebra are naturally separated by an intervertebral disc composed of collagenous and cartilaginous tissue. The intervertebral disc (IVD) primarily functions as a compression resistant member between the vertebrae whilst permitting a wide, but limited, range of motion.

The posterior portion of each vertebra includes bony and ligamentous elements such as the transverse processes, the spinous process, and the articular processes, together with a synovial joint known as the facet joint, also known as the zygapophysial joint or z-joint.

Where reference is made to anterior, posterior, superior, inferior, lateral and transverse, it is to be understood that the reference is made relative to a human body in an upright, fully erect stance.

A pair of adjacent vertebrae separated by an IVD is the fundamental anatomic unit of the spine, and is referred to as a motion segment. The biomechanical function of a motion segment is to transmit load whilst allowing a wide but limited range of motion.

Each motion segment has six degrees of freedom (associated with the planes and axes shown in FIGS. 2a and 2b), permitting high flexibility of the spine: (i) sagittal rotation (i.e. flexion which is a forward bending of the motion segment, and extension which is a backward bending of the motion segment) in the sagittal plane; (ii) sagittal translation (i.e. a translation of a part of the motion segment from front to back or vice versa) along the sagittal axis; (iii) transverse rotation (i.e. a torsional rotation of a part of the motion segment) in the transverse plane; (iv) transverse translation (i.e. a sideways translation of a part of the motion segment) along the transverse axis; (v) coronal rotation (i.e. a lateral bending of the motion segment to one side or another) in the coronal plane (also known as lateral rotation); (vi) coronal translation (i.e. a displacement of a part of the motion segment along the axis of the motion segment, resulting in an attraction or distraction of the adjacent vertebrae) along the coronal axis.

FIG. 2b shows the kinematic axes and planes. The kinematic transverse plane is a plane orthogonal to the kinematic sagittal plane which lies in the anatomic sagittal plane. The kinematic transverse plane is a plane that is tilted posteriorly about the anatomic transverse axis (i.e. when looking along the transverse axis from right to left, the tilt is anticlockwise) in the prone position by an angle equal to the wedge angle of the motion segment at issue. The kinematic coronal plane is orthogonal to the kinematic transverse plane and the sagittal plane (kinematic and anatomic).

Accordingly, hereafter where we refer to the transverse plane, we mean the kinematic transverse plane; where we refer to the coronal plane we refer to the kinematic coronal plane; and where we refer to the sagittal plane we refer to the kinematic and the anatomic planes, as they are equivalent.

Furthermore, the kinematic transverse axis is equivalent to the anatomic transverse axis. However, where we refer to the coronal axis, we refer to the kinematic coronal axis associated with the kinematic coronal plane and the sagittal plane; and where we refer to the sagittal axis, we refer to the kinematic sagittal axis associated with the kinematic transverse plane and the sagittal plane.

However, in a normal healthy spine some of these degrees of motion are coupled (see e.g. "Three Dimensional X-ray Analysis of Normal Movement in the Lumber Spine", Spine, 9, p. 294-297, 1984). For example, sagittal rotation is coupled to sagittal translation, and lateral bending is coupled to torsion (see e.g. "Axial rotation and lateral bending in the normal lumbar spine measured by three dimensional radiography", Spine, 9, p. 582-587, 1984), and to a much lesser degree to lateral translation. So, when a person bends forward, not only is the posterior angle between two adjacent vertebrae increased (i.e. flexion), but also the vertebrae translate relative to one another. Similarly, when a person bends sideways, not only is the lateral angle between adjacent vertebrae increased (i.e. lateral rotation), but the spine also twists along its length (i.e. axial rotation), and there may be a small lateral translation of one vertebra relative to the other.

The facet joint is formed in the posterior portion of a motion segment by the articulation of an inferior articular process of the superior vertebra with a superior articular process of the adjacent inferior vertebra. In a normal motion segment there are two such facet joints, one on either side of the sagittal midline of the motion segment, and their primary biomechanical function is to act as motion restraint, for example to restrain anterior shear translation and torsion.

When it is necessary to replace an IVD with a prosthetic IVD, the conventional method is to implant the prosthesis by insertion into the intervertebral disc space from the anterior of the motion segment, thereby leaving the facet joints to continue to act as motion restraint.

However, the highly invasive procedure of implanting the prosthesis to the spine through the abdominal cavity (or perhaps the thorax in the case of the thoracic spine) is both expensive, and clinically complex.

Even so, this procedure is undertaken because inserting a prosthetic IVD to the intervertebral space from the posterior of the motion segment necessitates the removal of the laminae (a laminectomy) to provide the surgeon with access to the IVD space for insertion of the prosthesis. A consequence of a laminectomy and/or a facetectomy is the removal of the facet joint, which leaves the motion segment with no significant natural motion restraint, in particular torsional motion restraint.

Indeed, although some prior art prostheses provide motion restraint in flexion/extension and perhaps even in lateral bend, they do not provide torsional motion restraint. For example, US2004/0243240 discloses an IVD having a non-articulating cylindrical block projecting from a convex surface into a recess of a nucleus which slides on the convex surface beneath it and which articulates with a concave surface located above it. The three piece device is limited in its range of flexion/extension and lateral rotation, but it is free to torsionally rotate.

Indeed, many prior art prostheses do not provide torsional motion restraint similar to that provided in a normal and healthy motion segment, and only limited motion restraint in other degrees of freedom. As such, insertion of these prostheses is not suited to be performed from the posterior of the spine, because with no significant motion restraint present in that motion segment, adjacent motion segments are left at risk of damage by increased-shear and/or torsional rotation of the motion segment receiving the prosthesis.

A lack of motion restraint is not the only problem to posterior insertion. The spinal cord presents an obstruction to the insertion of an IVD prosthesis from the posterior of the spine.

WO2004/107952 discloses an example of a bilateral prosthesis for insertion to the posterior of the spine. One of the embodiments is described as having convex arcuate bearing surfaces which are respectively accommodated by receptacles. The interaction between the bearing surfaces and the respective receptacles apparently allows for a limited posterior and anterior range of motion, whilst at the same time limiting lateral motion. However, there is no disclosure of a limit on the degree of torsional rotation, nor is it disclosed how the device permits lateral rotation whilst maintaining each respective bearing surface and receptacle pair as a bearing joint.

Another example of a bilateral prosthesis suitable for insertion to a spinal motion segment from the posterior aspect is given in US2005/0033435, which discloses a four piece bilateral split device having a spherical articulation joint split between the two lateral portions of the bilateral device. An object of the device of US2005/0033435 is said to be to provide ball-and-socket type movements in the motion segment. Accordingly no other shape of bearing joint is disclosed or suggested as being appropriate. Discussion of motion restraint is omitted.

A further example of a device suitable for insertion to the posterior of the spine is given in U.S. Pat. No. 6,692,495 which also discloses a four piece device. However, the four piece device is said to be arranged in use to form a geometrically coherent entity, such as an all-in-one piece. In this example, motion restraint is provided by an arrangement of rods located outside the IVD space and running along the length of the spine. The arrangement of rods is connected to the device in the IVD space by further rods which are in turn connected to fixation members attached to respective parts of the device.

In an alternative attempt to avoid the spinal cord, and perhaps the removal of one or both of the facet joints, some devices are intended to be inserted to an intervertebral space from a lateral direction or using a transforaminal approach. However, in these cases it is preferred, if not necessary, that at least one of the facet joints is left in place to act as a motion restraint. However, such approaches are not always suitable. Indeed, the L5/S1 cannot be easily approached laterally because the pelvis obstructs such an approach.

An example of an IVD prosthesis intended for transforaminal insertion is given in USA patent application publication number 2004/225365, which discloses a prosthesis of two-piece construction. The prosthesis includes a pair of vertebra contacting members, each member having a bearing face of spherical curvature in abutment with the bearing face of the other member, thereby forming a bearing joint. However, this device relies on the presence of at least one facet joint to provide torsional motion restraint, and restraint in some of the other degrees of freedom.

There are many examples of prostheses that attempt to provide articulation similar to that provided by a natural IVD. A first example of such a prosthesis is described in U.S. Pat. No. 6,179,874B, which discloses a range of two-piece prostheses having various bearing joints, and motion restraint features. However, the disclosed devices suffer from imparting a ball-and-socket type articulation to the motion segment, or the respective bearing surfaces of the inferior and superior parts of the device appear to give rise to relatively high bearing pressure at the bearing joint. Such prostheses may be suitable for anterior insertion to the spine.

Another example is the prosthesis described in International patent application publication number WO2004/064692, which discloses a prosthesis of two-piece construction. In that prosthesis a first body has a curved bearing surface for contact with a non-congruent curved bearing surface on a second body to form a bearing joint. The two bodies are able to translate relative to one another and rotate relative to one another. The prosthesis described in this International patent application does not appear to provide torsional motion restraint but limited lateral and sagittal motion restraint seems to be provided.

Another example is International patent application WO2005/011522 which discloses various prostheses considered suitable for posterior insertion. In one example, a four piece bilaterally split bearing device having a single curved bearing joint and simple non-articulating motion stop means is briefly illustrated. No details of how the bearing joint design or stop means approximates to natural motion segment kinematics is presented.

Yet another example is USA patent application no. US2004/0133281 which discloses a total disc implant (TDI) suitable for anterior insertion to the spine. In one embodiment, the TDI includes a bearing joint formed of two part-cylindrical oriented substantially perpendicular to one another, the respective part-cylindrical regions having contoured portions or flared ends, which engage at particular arrangements of the TDI. Such engagement is not over the entire range of motion of the device, however. Indeed, other examples of prosthesis disclosed as having non-articulating motion restraint are respectively given in WO2003/090649 and US2004/0176851.

In light of the above, a first aspect of the present invention provides an intervertebral disc prosthesis which includes means for limiting the extent of articulation of a first member relative to a second member, by providing limits of motion (i.e. motion restraint) similar to that provided by a facet joint of a motion segment.

As this aspect of the invention provides an articulating intervertebral disc prosthesis with motion restraint similar to that provided by a facet joint, but which simultaneously alleviates the bearing pressure on an articulating, and preferably a bearing, joint. An embodiment including this aspect of the invention could be used in a motion segment which has one or more damaged facet joints, or a motion segment which has been subject to a laminectomy, i.e. where the facet joints have been removed by excision of the laminae.

As such, this aspect of the present invention provides a prosthesis clearly suited for implantation to a motion segment with no facet joints, and could be inserted from the posterior aspect of the spine.

However, as discussed above, a complication of such an implantation procedure is the presence of the spinal cord running along the posterior region of the spine, in the spinal canal. A prosthesis extending across the lateral width of the motion segment cannot be inserted easily to the IVD space of the motion segment because the spinal cord obstructs the insertion.

Therefore, at its most general this first aspect of the present invention provides an articulating intervertebral disc prosthesis including a first member having a vertebra contacting portion, which in use contacts a first vertebra, and a bearing surface;

a second member having a vertebra contacting portion which in use contacts a second vertebra, and a bearing surface, which in use abuts the first member bearing surface to form a first bearing joint;

and motion restraint means adapted to provide articulation restraint of the bearing joints at predetermined limits of articulation similar to the natural motion restraint of a facet joint (i.e. a zygapophysial joint) of the spine; wherein the prosthesis is longitudinally split into two bodies so that the two bodies can be laterally separated, each body having a bearing joint, preferably an articulating joint, even more preferably an articulating bearing joint.

Preferably the motion restraint means includes first and second elements which are part of the first and second members respectively, as those elements co-operate to provide a second bearing surface. Most preferably, those elements co-operate to provide a second bearing surface over the entire range of motion (ROM) of the prosthesis. Advantageously, the load bearing is shared between the first bearing joint and the second bearing joint thereby reducing the bearing pressure on the first bearing joint.

The prosthesis is longitudinally split into two laterally spaced apart bodies so that each of the two bodies can be inserted into the spine separately. The first body can be inserted into the intervertebral space, to one side of the spinal cord, and the second body can be inserted to the intervertebral space on the other side of the spinal cord, thereby avoiding the obstruction caused by the spinal cord. This is a preferred arrangement for all aspects of the invention. However, in some cases, a prosthesis that is not split, i.e. one that is in two pieces (upper and lower, in use), or a prosthesis comprising more than two bodies may be used.

By longitudinally split it is meant that the prosthesis is suitably divided, preferably into two bodies, substantially along the anterior/posterior line of the device for insertion to the spine on either side of the spinal cord.

In this first aspect of the invention, at least one of the two bodies includes means, which provides motion restraint to limit the extent of the articulation of the articulating bearing joint or joints. Preferably, a motion restraint means is included in each of the two bodies.

However, it is also possible that the lateral separation of the two bodies, and the described formation of the articulating joints can be used in a prosthesis without motion restraint means. Such a prosthesis may be suitable for lateral, transforaminal or anterior insertion to the spine, where the posterior portion of the spine provides the motion restraint.

To provide motion restraint that is similar to the natural motion restraint provided by the facet joint, it is preferable that the motion restraint means limits translation of the first body first member and/or the second body first member relative to the respective second members to 4 mm maximum or less, preferably relative to the postulated natural centres of rotation of the lumbar motion segments. The natural lumbar motion segment centres of rotation have been postulated as having two distinct locations in the sagittal plane. The first is the flexion/extension rotation centre. This can be typically located approximately 1-2 mm below the superior end plate of the inferior vertebra of the motion segment and in the posterior third of that inferior vertebra (preferably approximately 10-12 mm in from the posterior portion of the anterior section) (see Instantaneous axes of rotation of the lumbar intervertebral joints' Pearcy & Bogduk, Spine, 13, p1003-1041, 1988). The second is the centre of rotation in lateral bending. This is typically located approximately 4-17 mm below the superior end plate of the inferior vertebra of the motion segment and in the posterior third of that inferior vertebra (preferably approximately 10-12 mm in from the posterior portion of the anterior section) (see "Discogenic Origins of Spinal Instability" Zhao et al., Spine, 30, No 23, p2621-2630, December 2005).

Preferably, the rotation of the vertebra contacting the first member about the vertebra contacting the second member should be limited in one or both of the anterior/posterior and lateral directions (i.e. in one or both of sagittal and coronal planes when the prosthesis is in use) and preferably the translation is limited in one or both of the anterior/posterior and lateral directions (i.e. along sagittal and transverse axes when the prosthesis is in use).

By translation it is meant, a linear distance travelled by a point on the first member bearing surface resolved to a plane, when the first member rotates about the second member. When in use the plane to which the linear distance is resolved is parallel to a transverse kinematic plane as shown in FIG. 2b which contains a postulated natural lumbar motion segment centre of rotation.

For the avoidance of doubt, by prone position, it is meant the position adopted by a person lying flat and face down, as though that person is to receive a prosthesis from the posterior aspect of the spine. This is to be contrasted with the supine position, which is the position adapted by a person lying flat and face up. Where a reference is made to the normal fully erect upright stance, this is the stance adopted by a person when standing erect, and each respective motion segment can be referred to as being in the neutral position, indicating that the spine is not in a state of flexion, torsion or lateral bend, and is posteriorly rotated relative to the sagittal anatomic axis as defined in FIGS. 2a and b.

Another aspect of the present invention provides an articulating intervertebral disc prosthesis which includes a first member having a vertebra contacting portion, which in use contacts a first vertebra, and a bearing surface;

and a second member having a vertebra contacting portion, which in use contacts a second vertebra, and a bearing surface, which in use abuts the first member bearing surface to form a first bearing joint;

wherein one or both of the first and second member bearing surface is shaped to provide a joint that exhibits kinematic characteristics similar to the natural characteristics of a intervertebral joint.

This aspect of the present invention provides an articulating IVD prosthesis, which may or may not include one or more of the other aspects of the present invention, having articulating bearing joints formed over two spatially separated bodies, each body preferably shaped or formed to approximate to a portion of a spheroidal bearing joint, so that when arranged such that the centre(s) of rotation of the portion of the bearing joint in each body is/are coincident, the two bodies can co-operate. It is preferred that the first body second member bearing surface is shaped to be or formed to approximate to a portion of the surface of the same spheroid of which the second body second member bearing surface is shaped to be a portion. Thereby, when in use, the first body articulating joint and the second body articulating joint fully co-operate to form articulating joint(s) which is/are split or divided. That is to say that the bearing surface of each of the first and second bodies is common to a particular spheroid but the bearing joint(s) of the first body and the second body is/are preferably non-contiguous.

Alternatively, a substantially spheroidal bearing joint can be formed over two laterally spaced bodies, such that when arranged the axes of rotation of that portion of the spheroidal bearing joint located in each body are coincident, and the two bodies can cooperate to permit articulation.

When we refer to a spheroidal bearing joint, we refer to an oblate spheroidal bearing joint whose articulating bearing surface can be shaped or formed to approximate to at least one substantially elliptical curve and has two major principal axes of equal length.

For clarity, the curvature of the second member bearing surface will now be discussed, but the discussion could be applied to the first member bearing surface.

This preferred aspect of the present invention thus provides a prosthesis in which the second member bearing surface is shaped to be or formed to approximate to a portion of a substantially spheroidal surface—preferably, an oblate spheroid, arranged so that the second member bearing surface is shaped or formed to approximate to a first substantially elliptical curve parallel to the sagittal plane, a second substantially elliptical curve parallel to the coronal plane and a third circular curve parallel to the transverse plane, all of which are mutually orthogonal to one another.

A second member bearing surface that is constructed to provide substantially elliptical curves parallel to the sagittal plane when in the spine, provides a bearing surface for an articulating joint, preferably a bearing joint, that results in a range of motion similar to that provided by the natural IVD, especially permitting the coupling of the translation and rotation in flexion/extension motion.

Advantageously, a second member bearing surface so shaped, or formed to approximate to an oblate spheroid, permits the axes of rotation, of the first member about the second member when moving in flexion/extension, and lateral bending, to pass through the postulated centres of rotation of the natural lumbar motion segment.

Another aspect of the present invention is provided by an articulating intervertebral disc prosthesis including
  a first member having a vertebra contacting portion which in use contacts a first vertebra and a bearing surface;
  a second member having a vertebra having a contacting portion, which in use contacts a second vertebra, and a bearing surface, which in use abuts the first member bearing surface to form a bearing joint;
  wherein the prosthesis is divided into two bodies each having a portion of the bearing joint, and wherein the first body first member bearing surface partially conforms to the first body second member bearing surface. Preferably, the second body first member bearing surface partially conforms to the second body second member bearing surface.

Preferably, the first body second member is arranged, relative to the second body second member, so that the portion of a spheroid of which the first body second member bearing surface is shaped to be a portion, or is formed to approximate to be a portion, has geometrical centres coincident with the portion of a spheroid of which the second body second member bearing surface is shaped to be, or formed to approximate to be, a portion. In effect the spatially separated bodies of the prosthesis each have a bearing joint which is formed, and is capable of being arranged, to be portions of the same shape.

Yet another aspect of the present invention provides an articulating intervertebral disc prosthesis which includes a first member having a vertebra contacting portion, which in use contacts a first vertebra, and a bearing surface;
  and a second member having a vertebra contacting portion, which in use contacts a second vertebra, and a bearing surface, which in use abuts the first member bearing surface to form a first bearing joint;
  wherein one or both of the first and second member bearing surface is shaped to provide a joint that exhibits functional characteristics similar to those exhibited by a natural intervertebral joint, and that provides a substantially conforming bearing surface to reduce the wear-rate of the bearing surfaces.

To achieve this functional similarity, and the ameliorated wear-rate, the second member bearing surface and/or the first member bearing surface, when viewed in a first section, is preferably shaped to include at least a portion of a first radial arc approximate to a portion of a substantially elliptical curve or locus, and when viewed in a second section which is orthogonal to the first section mentioned above, the first and/or the second member bearing surface are further shaped to include a second radial arc approximate to a portion of a substantially elliptical curve or locus.

It is preferred that a section made parallel to the coronal plane is made parallel to the kinematic coronal plane. Accordingly, the section is made to the anatomic coronal plane at an angle of between 0° and 15° (rotated posteriorly). However, the angle may be more preferably between 4° and 10° and even more preferably between 6 and 8°. The angle is most preferably either 6° or 8°.

Another aspect of the present invention provides motion coupling stop means, permitting the coupling of motions within the motion segment similar to that of the natural motion restraint means provided by a fully functioning and healthy motion segment. At its most general this aspect of the present invention proposes an articulating intervertebral disc prosthesis including
a first member having a vertebra contacting portion, which in use contacts a first vertebra, and a bearing surface;
  a second member having a vertebra contacting portion, which in use contacts a second vertebra, and a bearing surface, which in use abuts the first member bearing surface to form a first bearing joint;
  and motion coupling stop means;
  wherein
  the motion coupling stop means is arranged to provide a predetermined limit of combined lateral and torsional rotation of the first member relative to the second member, at a predetermined limit of extension of the first member relative to the second member.

Although it is preferable that this aspect of the present invention is used together with the at least one of the other aspects described herein, such use is not essential.

Preferably, in use, the motion coupling stop means is arranged such that when the predetermined maximum limit of extension of the motion segment is reached, the stop means restrains further extension, but the motion coupling stop means permits a torsional rotation of the vertebrae of the motion segment relative to one another when the vertebrae are rotated laterally around one another in a coronal plane.

In a preferred embodiment, the arrangement of the motion coupling stop means is alternatively, or additionally, arranged such that when the predetermined maximum limit of, flexion of the motion segment is reached, the stop means restrains further flexion, but the motion coupling stop means permits a torsional rotation of the vertebrae of the motion segment relative to one another when the vertebrae are rotated laterally around one another in the coronal plane.

The different (fully functional) motion segments of the spine naturally exhibit different ranges of motion and different limits of motion. Therefore, it is desirable to provide prosthetic IVDs with different characteristic ranges of motions and motion restraint limits for use in the different motion segments.

In a prosthesis intended to be used in the L5/S1 motion segment of the spine, it is preferable that when in use the motion coupling stop means permits, at a maximum predetermined flexion and/or extension, a coupling of the lateral rotation and the torsional rotation of the vertebrae of a motion segment, a progressive degree of torsional rotation up to a maximum of 1°. Preferably, a maximum of 0.4° is permissibly coupled with a progressive degree of lateral rotation up to a maximum of 1°. Preferably, the limit of maximum flexion is 13° from the normal upright stance of the recipient of the prosthesis.

In an alternative prosthesis intended to be used in the L3/L4 motion segment, the motion restraint means is arranged to provide at a predetermined maximum flexion and/or extension of the L3/L4 motion segment a permissible progressive torsional rotation of 2° coupled to a progressive lateral rotation of 5°. Preferably, the limit of maximum flexion is 13° from the normal fully erect upright stance of the recipient of the prosthesis.

In another alternative prosthesis intended for use in the L4/L5 motion segment, it is preferred that the motion restraint means (when in place in the spine) permits, at a predetermined maximum flexion of the motion segment, a coupling of lateral rotation of the first member to a torsional rotation of the first member relative to the second member, so that a torsional rotation of up to 1° is permitted for a progressive lateral rotation of up to 3° Preferably, the limit of maximum flexion is 13° from the normal upright stance of the recipient of the prosthesis.

The limit of flexion from an upright stance, has been shown in some cases (see "Three dimensional X-ray analysis of normal movement in the lumbar spine" Spine, 9, p 294-297, 1984; and, "Axial rotation and lateral bending in the normal lumbar spine measured by three dimensional radiography" Spine, 9, 582-587, 1984) to be 14° for the L5/S1 motion segment, and the above described L5/S1 prostheses may be limited to such a range; however, it is preferable that a prosthesis for use in the L5/S1 motion segment is limited to a maximum flexion of 13° from an upright stance. The limit of flexion from an upright stance, has been shown to be 15° for the L4/L5 motion segment, and the above described L4/L5 prostheses may be limited to such a range; however, it is preferable that a prosthesis for use in the L4/L5 motion segment is limited to a maximum flexion of 13° from an upright stance. The limit of flexion from an upright stance has been shown to be 13° for the L3/L4 motion segment, and the above-described L3/L4 prostheses are preferably limited to such a range.

Furthermore, preferably, the first and second member vertebra contacting portions are angled, or tapered, to match the wedge angle of the motion segment to which the relevant prosthesis is intended to be inserted in the prone position. Therefore, in a prosthesis intended for use in the L3/L4 and L4/L5 motion segment, the angle of taper of the first and second member vertebra contacting portions is preferably 6°; whereas in a prosthesis intended for use in the L5/S1 motion segment the angle of taper of the first and second member vertebra contacting portions is preferably 8°.

Yet another aspect of the present invention provides an articulating intervertebral disc prosthesis that includes a feature helping to reduce shear forces at the bearing interface. Such a prosthesis includes a first member having a vertebra contacting portion, which in use contacts a first vertebra, and a bearing surface; and
a second member having a vertebra contacting portion, which in use contacts a second vertebra, and a bearing surface, which in use abuts the first member bearing surface to form a first bearing joint;
wherein
the second member bearing surface is shaped, or is formed to approximate, to include at least a portion of a first substantially spheroidal curved surface, which surface is preferably adapted so that when in use the spheroid of which the second member bearing surface is shaped to be, or is formed to approximate to be, a portion, is effectively posteriorly rotated about the postulated centre of rotation in flexion/extension by an angle equal to the wedge angle of the motion segment, to which the prosthesis is intended to be inserted. The effect of this posterior rotation is that the force resolution of the compressive thrust is reduced, particularly in the anterior direction. As such, this arrangement of the second member bearing surface reduces the interfacial shear forces at the bearing joint, thereby decreasing wear rate and improving the rate of vertebrae to implant osseo-integration and fixation.

Although it is preferable in one or more aspects of the present invention that the bearing joint can be spheroidal it is not essential.

The second member bearing surface and/or the first member bearing surface, when viewed in section, can be preferably shaped to include or constructed from at least a portion of a first substantially elliptical curve or locus. The curve or locus is substantially elliptical in that the change in its radius of curvature is substantially similar to that of at least a portion of an ellipse. However, a mathematical formula defining an ellipse may not describe the curve precisely. Indeed, the curve may be a splined curve or a radial arc approximation to the elliptical curve.

For the avoidance of doubt, we state here that when we refer to an ellipse, we preferably refer to a non-circular ellipse; we also state that when we refer to a substantially elliptical curve we preferably refer to a non-circular substantially elliptical curve. In effect, an ellipse is formed around two principal axis, one major and one minor. Therefore, to be a non-circular ellipse, the major and minor axes are not of equal length.

The curve is shaped as described above, because an ellipse, or a substantially elliptical curve, can be centred on the postulated natural centres of motion described above, and provide articulation about those centres. In contrast a sphere centred on either of the postulated natural centres of rotation would have a relatively short radius and thus a very tight curvature results in a large degree of rotation for a small amount of translation. In contrast, an ellipse can be centred on the postulated natural centre of rotation, and yet still provide a region of relatively large curvature.

If the prosthesis is adapted so that the second member bearing surface, and/or the first member bearing surface can be constructed from a substantially elliptical curve, when viewed in section in a first direction, it is preferable that the direction is such that when the prosthesis is in place between two adjacent vertebra, that the radii of curvature of the substantially elliptical curve are substantially parallel to the sagittal plane, or to the coronal plane.

It is preferable that the substantially elliptical curve is at least a portion of an ellipse.

For clarity only the curvature of the second member bearing surface will be discussed hereafter. However, the description of the curvature of the second member bearing surface is also applicable to the first member bearing surface.

It is preferred that the second member bearing surface is further constructed from a second substantially elliptical curve when viewed in a second section in a second direction, the second direction in which the second section is made being a different direction to the direction in which the first section is made.

It is also preferred that the radii of curvature of the second substantially elliptical curve are orthogonal to the radii of curvature of the first substantially elliptical curve. It is also preferred that the second member bearing surface is shaped so that the radii of curvature of the first, and of the second substantially elliptical curves are parallel respectively to the sagittal plane and the coronal plane when the prosthesis is in place between two adjacent vertebrae of a motion segment.

Preferably, both the first and second substantially elliptical curves are portions of ellipses. It is possible that the two principal axes of the first ellipse are the same length as the two principal axes of the second ellipse, i.e. the first and second portions of ellipses are of identical shape, but oriented differently, and preferably orthogonally.

It may be preferred that the second member bearing surface is further constructed from a third substantially elliptical curve when viewed in a third section in a third direction. Preferably, the radii of curvature of the third substantially elliptical curve are formed to be orthogonal to the radii of curvature of the first and/or the second substantially elliptical curves. In this embodiment, it is also preferable that the radii of curvature of the first substantially elliptical curve are orthogonal to the radii of curvature of the second substantially elliptical curve.

It is preferred that the third substantially elliptical curve is a portion of an ellipse or circle and even more preferred that the first and second substantially elliptical curves are all portions of ellipses, thereby constructing the second member bearing surface to be a portion of an ellipsoidal surface.

It is preferable that the second member bearing surface can be formed from radial arc approximations to substantially elliptical curves, the radii of curvature of which are parallel to the transverse plane, sagittal plane and coronal plane respectively when the prosthesis is in place in the spine.

It is preferable that the first ellipse is formed so that when the prosthesis is in place in a spine, a principal axis of the ellipse is angled relative to the sagittal axis.

Preferably, a principal axis is angled by 15° or less to the second member vertebra contacting portion. Even more preferably the angle is 10° or less, but the angle could be 5° or less. It is preferred that it is the major principal axis that is angled to the second member vertebrae contacting portion by 15° or less, or 10° or less, or 5° or less.

To prevent movement of the first member of the prosthesis relative to the first vertebra, and to prevent movement of the second member of the prosthesis relative to the second vertebra, a keel projecting from the first member vertebrae contacting portion is received in a keel-way formed in the face of the first vertebra that abuts the first member; likewise a keel extending from the second member vertebra contacting portion is received by a keel-way formed in the face of the second vertebra that abuts the second member.

Each keel-way in the first vertebra is preferably formed to be opposite to a keel-way formed in the second vertebra when the spine is in the prone position. To form a keel-way respectively in the first and second vertebrae accurately, another aspect of the present invention proposes a first chisel having a pair of tines projecting from one end, the tines being spaced apart from one another. The tines are adapted so that the opposing faces of the tines are chamfered so that the opposing faces of the tines converge along the axis of the chisel in a direction away from the tine points.

To create a planar floor in one keel-way in, say, the first vertebra, and a planar ceiling in the opposite keel-way, say in the second vertebra, the tines are spaced apart from one another across the broad width of the chisel blade, to a distance greater than the separation of a pair of adjacent vertebrae.

In an alternative chisel which is intended, in use, to create a pair of planar walls in either or both of the keel-ways, the tines are spaced across the narrow depth of the chisel and preferably the face of each tine that faces the other tine converges to meet the other tine, forming a general V shape, when seen in section made parallel to the long axis of the chisel and to the narrow width of the chisel.

Where a plurality of keel-ways is required to be formed in one vertebra, it is preferable that the plurality of keel-ways formed in the vertebra is accurately spatially aligned.

In the case of a single body prosthesis (e.g. a body comprising first and second members, which abut at an articulating joint) the alignment of the plurality of keels in the first, or the second, vertebra is preferable to permit easy and accurate insertion of the prosthesis to the motion segments.

More crucially, in a prosthesis having two laterally spaced bodies, the lateral spacing of the two bodies is critical. Therefore, another aspect of the present invention provides a chisel alignment instrument, which includes a first guide means for guiding a chisel blade, a second guide means for guiding a chisel blade, wherein the first and second guide means are distally separated by a spacer.

The first and second guide means are thus separated by a predetermined amount. A modified alignment instrument might include an adjustable spacer for varying the separation of the first and second guide means to a predetermined extent, preferably to 15-30 mm but more preferably to 24 mm.

In use, the alignment instrument is inserted to the IVD space, say from the posterior aspect of the spinal column, and the first and second guide means act as separating means to drive apart the first and second vertebrae to a separation or distraction predetermined by the depth of the guide means. The guide means preferably include a bullet-nosed, or wedge shaped portion located at the end of insertion of the instrument, to help drive apart the vertebrae.

Each guide means is modified so that a portion of the guide means is removed to expose the passage defined by the guide means, i.e. to create an aperture. The passage is preferably exposed at a region of the guide means distal to the aperture of the guide means that receives the chisel. The portion that is removed from each guide means is in the region of the instrument intended to be inserted between the vertebrae of a motion segment.

Preferably, to allow a plurality of keel-ways to be formed in the first and second vertebra without removing the alignment instrument, a portion of each of the guide means is removed on opposite sides of each guide means, so that an appropriately broad chisel located in the guide means, when translated axially along the entire length of the passage is at least partially exposed and at least a portion of the cutting edge of the chisel is capable of impacting a portion of the first and second vertebrae that are spaced apart by the guide means. Preferably, the portion of the first guide means that is removed is the same as the portion of the second guide means that is removed.

The spacer could be a U-shaped member, allowing each of the guide means to be inserted to the appropriate IVD space of a motion segment from the posterior aspect of the spine, one to either side of the spinal cord. The U-shaped spacer member obviates the obstruction caused by the spinal cord.

Once the keel-ways have been formed in either or both of the first and second vertebrae, the prosthesis must be accurately inserted to the IVD space, by aligning keels projecting from the prosthesis with the keel-ways formed in the vertebra or vertebrae.

Therefore, another aspect of the present invention proposes an insertion instrument that allows the accurate insertion of keels, projecting from the first and/or second member vertebra contacting portions, to keel-ways pre-formed in the first and/or second vertebrae. The insertion instrument prevents the articulation of the first member relative to the second member during insertion.

The insertion instrument includes a shaft, along the length of which a passage is defined having an opening at one end of the shaft; a rotatable threaded spindle disposed in the shaft protruding through the opening for threaded engagement with a complementary threaded recess formed in a first articulating member, which is a part of an articulating prosthesis; and engagement means for coupling the shaft to a second articulating member which is a part of an articulating prosthesis; wherein the engagement means only restricts movement of the second member to a direction parallel to the long axis of the shaft.

It is preferred that the engagement means is a shaped key projecting from the end of the shaft adjacent the opening through which the rotatable threaded spindle protrudes, for engagement with a complementary shaped recess formed in the second member of the articulating prosthesis.

Alternatively, the above-described engagement means could be swapped around so that a shaped recess, formed in the shaft adjacent the opening through which the rotatable spindle protrudes, receives a complementary shaped projection formed on the second member of the articulating prosthesis.

Of course, the arrangement of the threaded recess and the complementary engagement means could be such that the threaded recess is formed in the second member, and the complementary engagement means is formed on the first member.

Preferably, the shaped key, and keyhole, are shaped to prevent rotation of the member associated with the engagement means around an axis parallel, and perpendicular, preferably, to that of the long axis of the shaft. Preferably, the key or key-hole is shaped so that the appropriate member can only be coupled to the shaft in one orientation.

To keep the prosthesis in the correct orientation and to facilitate expedited mounting of the prosthesis onto the implantation instrument, another aspect of the present invention provides a cartridge for housing one or more prostheses. The cartridge includes a housing having at least one recessed shaped to receive a prosthesis, or one body of a prosthesis, for example a body of the split prosthesis described in the present invention. The cartridge preferably includes storage keel-ways for receiving any keels included in the prosthesis.

Another aspect of the present invention provides a method of insertion of a prosthesis to the IVD space of a motion segment. At its most general, a procedure, or method, of inserting the IVD prosthesis to the IVD space from the posterior aspect of the spine includes: performing a full or partial facetectomy and/or laminectomy to provide access to the IVD space, preferably performing a bilateral facetectomy with retention of the midline anatomical structures; performing a discectomy to remove the natural IVD optionally; inserting to the vertebrae of the motion segment a set of pedicle screws; inserting an instrument to the IVD space to distract apart the adjacent vertebrae of a motion segment; cutting at least one keel-way in at least one of the vertebrae of the motion segment that will receive the IVD prosthesis; preferably, mounting a disc prosthesis to an insertion instrument, preferably a disc prosthesis and an insertion instrument each according to at least one aspect of the present invention; using the insertion instrument to insert the disc prosthesis to the IVD space from the posterior aspect of the spine, so that a keel projecting from the disc prosthesis abuts the region of at least one vertebra that partly defines a keel-way; compressing the vertebrae of the motion segment together by use of the pedicle screws or more preferably adjacent spinous processes, thereby forcing the keels into the keel-ways; using an impactor to drive the prosthesis forward (i.e. from posterior to anterior) in each keel-way to achieve firm location. Where the prosthesis is a bilateral prosthesis, i.e. a device including two bodies, one to be inserted to either side of the spinal cord, the forming of the keel-ways is performed using an alignment instrument to provide accurate spatial separation and alignment of the keel-ways.

Embodiments of the present invention will now be described by way of example with references to the accompanying figures, in which:

FIG. 6b is a plan view of a pair of members forming part of a prosthesis, according to the present invention, intended for use in the L3/L4 or L4/L5 motion segment together with the members shown in FIG. 6a;

FIG. 7b is a plan view of a pair of members forming part of a prosthesis, according to the present invention, intended for use in the L5/S1 motion segment together with the members shown in FIG. 7a;

FIG. 8b is a plan view of a pair of members forming part of a prosthesis, according to the present invention, intended for use in the L3/L4 or L4/15 motion segment together with the members shown in FIG. 8a;

FIG. 9b is a plan view of a pair of members forming part of a prosthesis, according to the present invention, intended for use in the L5/S1 motion segment together with the members shown in FIG. 9a;

FIG. 11c shows a threaded spindle, which is part of the instrument of FIG. 11a;

FIG. 12 shows a prosthesis according to the present invention attached to the implant instrument of FIG. 11a;

Figure 3A:
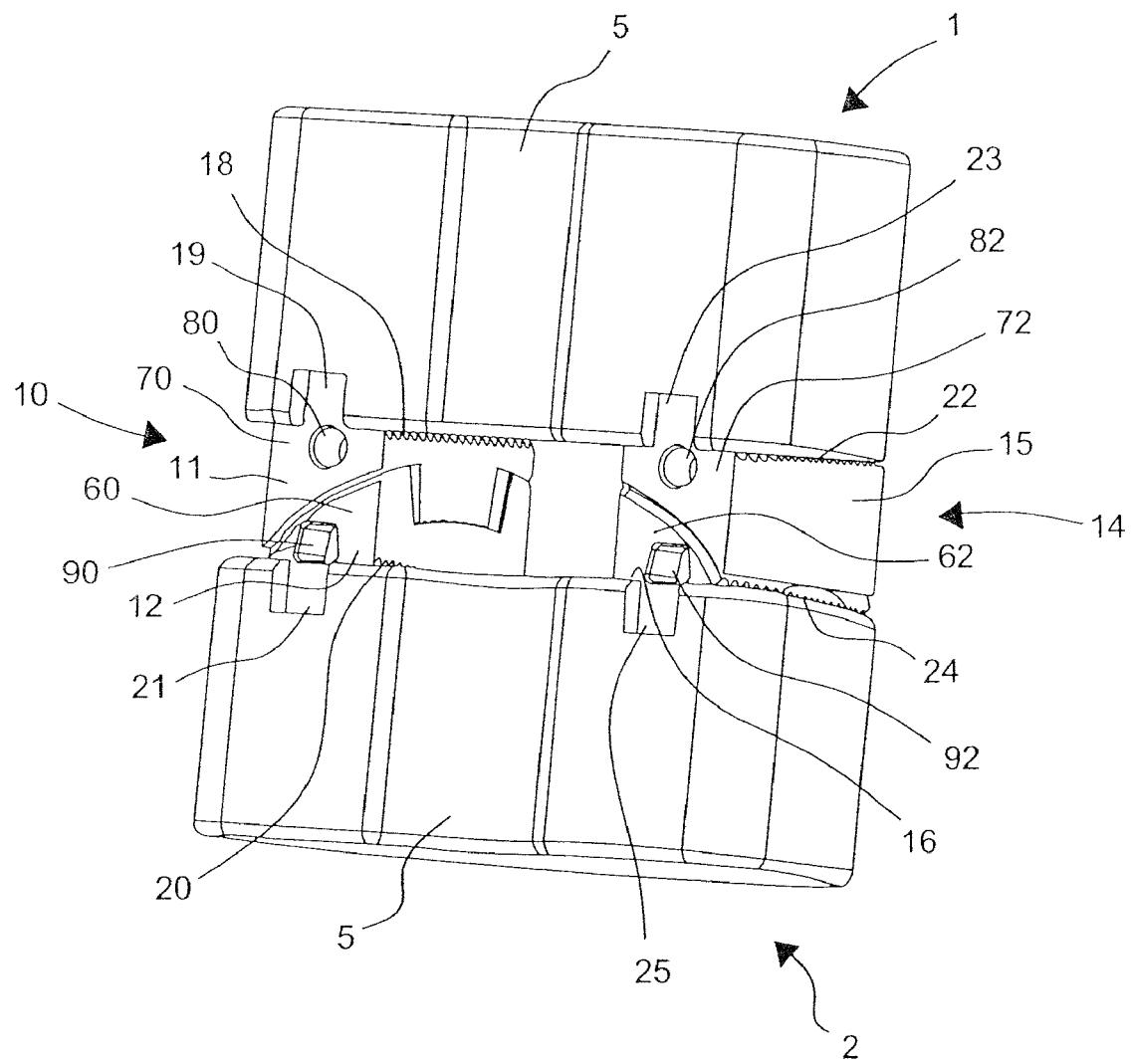
FIG. 3a is an oblique posterior view of an embodiment of the present invention positioned between adjacent vertebrae.

FIG. 3a shows an articulating intervertebral prosthesis according to the present invention, which is of four-piece construction and which is shown sandwiched between a first vertebra 1 and a second vertebra 2, having a spinal canal 5. The embodiment described here is formed to have a first body 10 and a second body 14 spaced laterally from the first body 10. The first body 10 includes a first member 11 and a second member 12, and the second body 14 includes a first member 15 and a second member 16.

The first and the second members are preferably formed from polyarylketone composite, however, any suitable "state of the art" plastic, rubber, composite, alloy or ceramic could be used. Preferably at least one of the bearing surfaces is coated with diamond-like carbon coating.

In an alternative embodiment (not shown), one of the first member bearing surface and the second member bearing surface of one of or both the first body and the second body could be made from a deformable material, so that the compression created at the bearing surface when the user is in an upright fully erect stance moulds at least one of the deformable bearing surfaces to conform to an opposing non-deformable bearing surface.

FIG. 3a shows the preferred arrangement of the prosthesis with respect to the vertebrae, such that the first vertebra 1 is the superior vertebra and the second vertebra 2 is the inferior vertebra. An alternative embodiment is shown in FIG. 3d.

The embodiment shown in FIG. 3a is intended for insertion to an intervertebral space from the posterior aspect of a motion segment, i.e. through the back of the recipient of the prosthesis, and as such the device is divided longitudinally (along the sagittal axis when in the spine) into two laterally spaced (along the transverse axis when in the spine) bodies 10, 14 for insertion to the intervertebral space—one to each side of the spinal cord running along the canal 5.

Figure 3B:
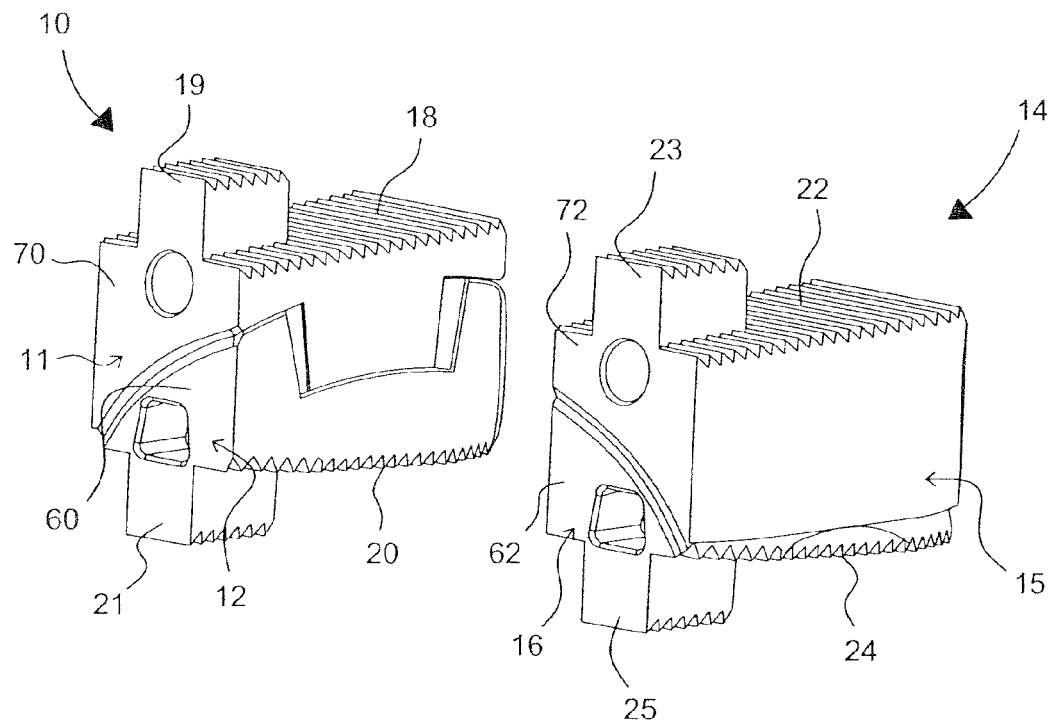
FIG. 3b is an oblique posterior view of an embodiment of the present invention.
Figure 3C:
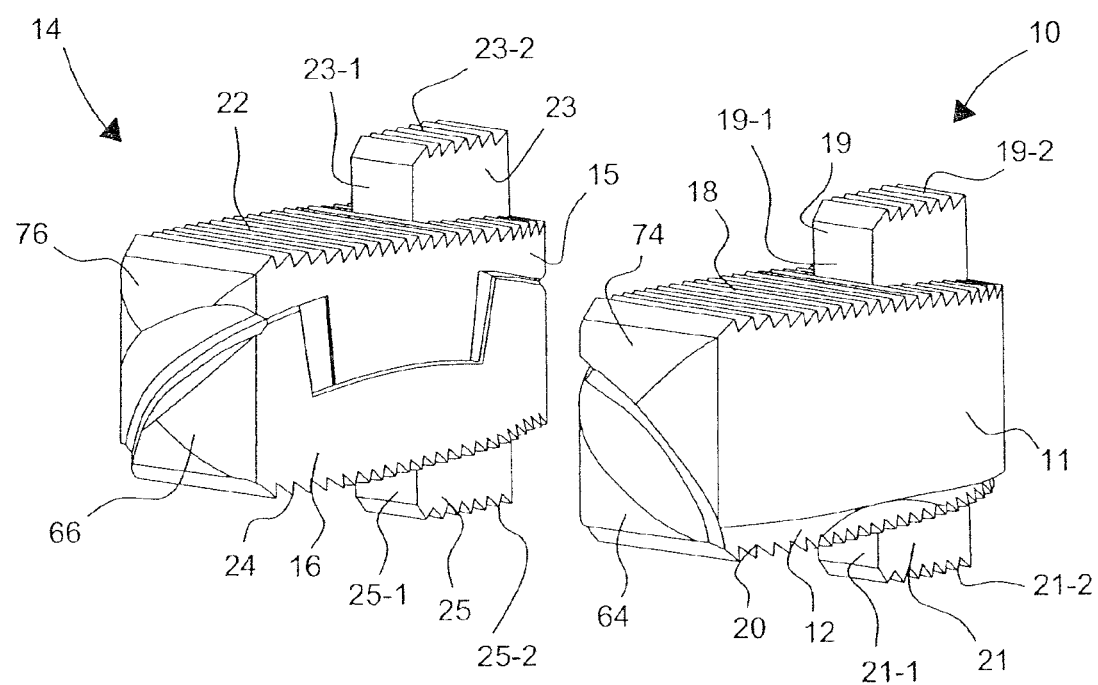
FIG. 3c is an oblique anterior view of an embodiment of the present invention.
Figure 3D:
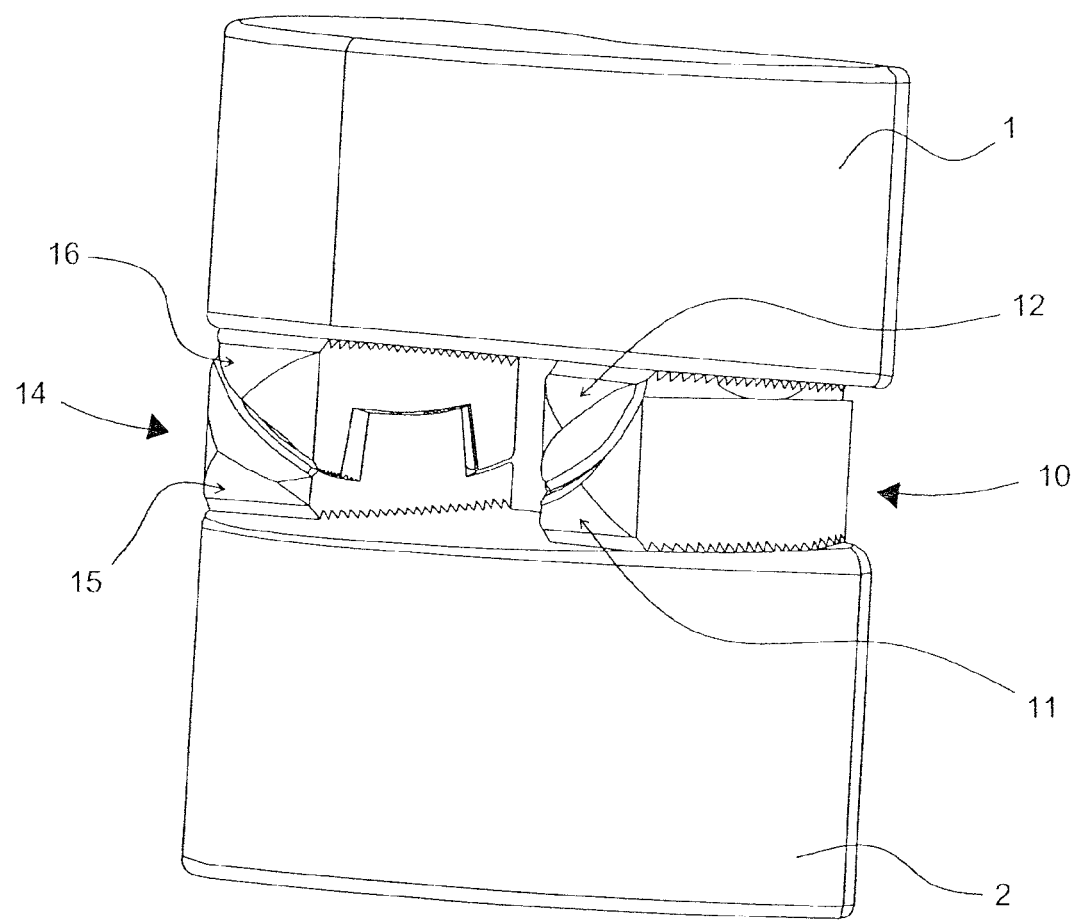
FIG. 3d is an oblique anterior view of an alternative embodiment of the present invention positioned between adjacent vertebrae.

FIG. 3b and FIG. 3c show the present embodiment in the absence of the two vertebrae. The first body first member 11 has a first vertebra contacting portion 18, and the first body second member 12 has a second vertebra contacting portion 20. Likewise, the second body first member 15 has a first vertebra contacting portion 22, and the second body second member portion 16 has a second vertebra contacting portion 24.

The vertebra contacting portions 18, 20, 22, 24 are profiled in this embodiment to be a buttress-thread type ridged surface to prevent translation of the prosthesis along the posterior to anterior axis when the prosthesis is in place in the spine and in use. However, this is not the only means of preventing such translation, there are many known solutions in the art, for example other profiled surfaces such as shark-tooth profile, knurled saw-tooth profile, or pyramidal profile.

Preferably, the vertebra contacting portions are coated with an osseointegrative material, such as Hydroxyapatite (HAP).

In the preferred embodiment, each of the vertebra contacting surfaces 18, 20, 22, 24 includes a projecting keel 19, 21, 23, 25 (respectively) extending towards the vertebra to which the respective surface contacts. Each of these keels is received in a keel-way formed in the respective vertebra surface that abuts the vertebra contacting portion.

In a more preferred embodiment, the vertebra contacting portions 19, 21, 23 and 25 of the projecting keels can be tapered, to improve fit and location to their respective receiving keel-ways following posterior insertion and intraoperative compression. In effect, each respective leading edge 19-1, 21-1, 23-1 25-1 can be chamfered. Likewise, surfaces 19-2, 21-2, 23-2 and 25-2 can be alternatively or additionally angled.

The keel-way is a channel formed in the vertebra by removing a portion of the vertebra itself. This can be done by chiselling, drilling, cutting or in any way known in the art. Preferably the keel-way is a channel formed by chiselling using the tools described below.

Preferably, the keel-way is formed so that its width (i.e. the lateral dimension of the keel-way), is slightly less than the width of the keel, to provide an interference fit. It is also preferable that the height of the keel-way (i.e. the dimension of the keel-way along the axis of the spine) is made slightly less than the height of the keel—the keel-way deforming slightly under compression, so that the (first or second) member vertebra contacting portion abuts the vertebra.

The engagement of the keel and keel-way prevents lateral movement and torsional movement of the member from which the keel projects relative to the vertebra to which the member contacts.

Figure 4:
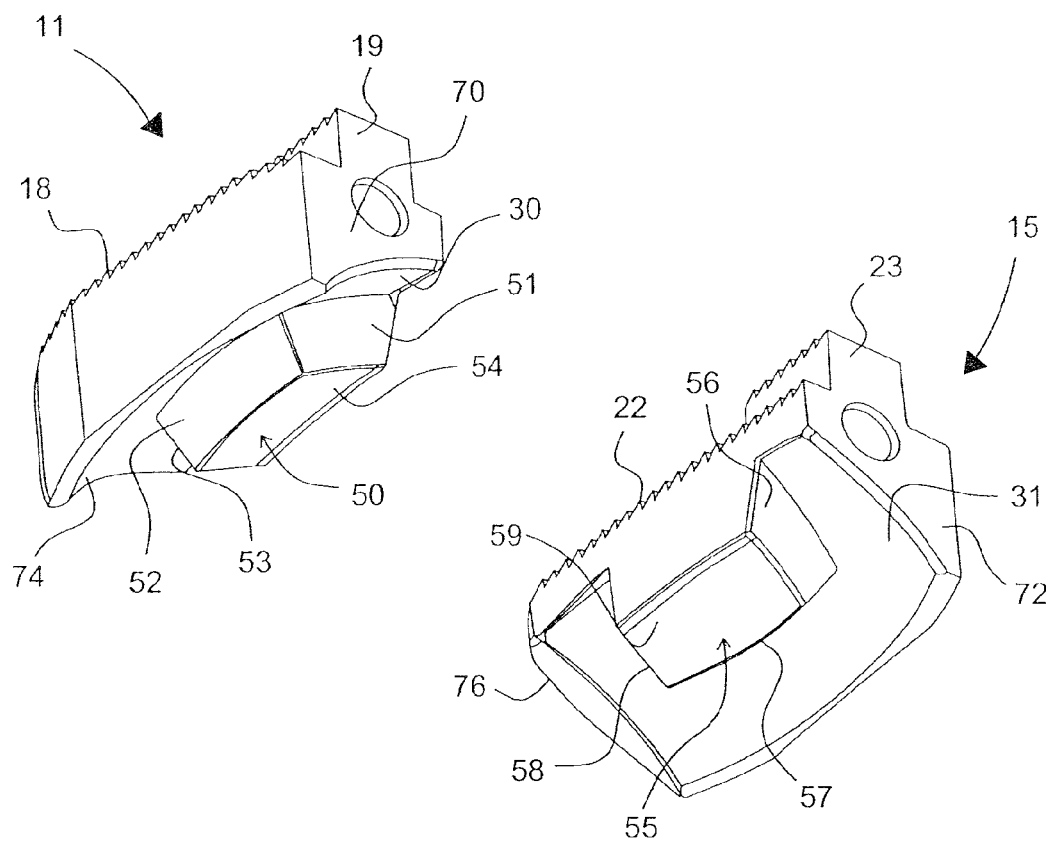
FIG. 4 is an oblique posterior view of a pair of members forming a part of a prosthesis according to the present invention.

Each of the first members 11, 15 has a bearing surface 30, 31 (respectively) as shown in FIG. 4. In this preferred embodiment each bearing surface is formed to approximate to a portion of an oblate spheroidal surface The first and second body first member bearing surfaces 30, 31 abut the respective second member bearing surfaces 35, 36 shown in FIG. 5.

In this preferred embodiment, the second member bearing surfaces 35, 36 are also formed to approximate to a portion of an oblate spheroidal surface.

As in the present embodiment, it is preferred that the surface of which the first member bearing surface is a portion, is a portion of the same shape of which the second member bearing surface is a portion.

It is even more preferred, as shown in FIG. 3*a*, that the first body 10 and the second body 14 are arranged in the spine so that the centre(s) of rotation of the second member bearing surface of each of the first and second body are coincident.

A prosthesis intended for use in an L3/L4 motion segment exhibits a flexion/extension rotation in the sagittal plane when located in the spine of a maximum of 13° rotation of the first member around the second member. Preferably, the 13° rotation is flexion rotation from the normal fully erect upright stance. Such a prosthesis also preferably exhibits a 3.4 mm anterior translation coupled to the flexion rotation of 13°. A preferred prosthesis for use in the L3/L4 motion segment also exhibits a maximum 5° lateral rotation of the first member about the second member, in the coronal plane when in the spine; and preferably the prosthesis exhibits a 2° axial rotation coupled with the maximum 5° lateral rotation; and preferably, the prosthesis exhibits a 1.9 mm lateral, or transverse, translation of the first member relative to the second member.

A preferred embodiment of such a prosthesis intended for use in the L3/L4 motion segment, is formed so that the second member bearing surface approximates to a portion of a spheroidal surface, e.g. an oblate spheroid, as constructed and detailed in FIGS. 20, 21*a*, 21*b* and 21*c* and Table II.

A prosthesis, intended for use in an L4/L5 motion segment exhibits a flexion/extension rotation in the sagittal plane when located in the spine of a maximum of 13° rotation of the first member around the second member. Preferably, the 13° rotation is a flexion rotation from the normal fully erect upright stance. Such a prosthesis also preferably exhibits a 3.4 mm anterior translation coupled to the flexion rotation of 13°. A preferred prosthesis for use in the L4/L5 motion segment also exhibits a maximum 3° lateral rotation of the first member about the second member, in the coronal plane when in the spine; and preferably the prosthesis exhibits a 1° axial rotation coupled with the maximum 3° lateral rotation; and preferably, the prosthesis exhibits a 1.2 mm lateral, or transverse, translation of the first member relative to the second member.

A preferred embodiment of such a prosthesis intended for use in the L4/L5 motion segment, is formed so that the second member bearing surface approximates to a portion of a spheroidal surface, e.g. and oblate spheroid, as constructed and detailed in FIGS. 20, 21*a*, 21*b* and 21*c* and Table II.

A prosthesis, intended for use in an L5/SS motion segment exhibits a flexion/extension rotation in the sagittal plane when located in the spine of a maximum of 136 rotation of the first member around the second member. Preferably, the 13° rotation is a flexion rotation from the normal fully erect upright stance. Such a prosthesis also preferably exhibits a 3.0 m anterior translation coupled to the flexion rotation of 13°. A preferred prosthesis for use in the L5/S1 motion segment also exhibits a maximum 1° lateral rotation of the first member about the second member, in the coronal plane when in the spine; and preferably the prosthesis exhibits a 0.4° axial rotation coupled with the maximum 1° lateral rotation; and preferably, the prosthesis exhibits a 0.4 mm lateral, or transvers, translation of the first member relative to the second member.

A preferred embodiment of such a prosthesis intended for use in the L5/S1 motion segment, is formed so that the second member bearing surface approximates to a portion of a spheroidal surface, e.g. an oblate spheroid, as constructed and detailed in FIGS. 20, 21*a*, 21*b* and 21*c* and Table II.

Advantageously, this arrangement of the first and second member bearing surfaces, gives rise to coincident axes of rotation which pass through the postulated natural centres of rotation of a normal motion segment, in the sagittal plane and coronal plane.

The anterior portions 64, 66 of the second members and 74, 76 of the first members are shaped to make the insertion of each of the parts of the prosthesis to the intervertebral space easier. The preferred embodiment presented here includes bullet-shaped anterior portions, but any shape that acts to separate the vertebrae as the prosthesis is inserted would be suitable, for example a wedge-shape, a portion of a sphere, a portion of an ellipsoid or spheroid, or any other arcuate or non-arcuate shape that is capable of resolving a distracting thrust force along the longitudinal axis into a force for separating the vertebrae of a motion segment as the prosthesis is thrust into the IVD space.

The first body first member posterior portion 70 has, and in this preferred embodiment, the second body first member 72 has, respectively, a first body threaded recess 80 and a second body threaded recess 82. These threaded recesses 80, 82 are a preferred feature of a prosthesis inserted to a motion segment using the implant instrument according to one of the aspects of the present invention. Such an instrument is described below in detail.

Moreover, in this preferred embodiment the first body second member posterior portion 60 and the second body second member anterior portion 62 include, respectively, a shaped keyhole 90, 92. These keyholes are intended to receive a complementary shaped key projecting from the implantation instrument which is an aspect of the present invention, and which instrument is described below in detail.

It is preferable that when the user is in a normal upright stance, that the first body first member posterior position 70 is flush with the first body second member posterior portion 60; and preferably that the second body first member posterior portion 72 is flush with the second body second member portion 62. The first member first body portion 70 should preferably be substantially in the same plane as the second body first member posterior position because the instruments described below, when used, provide for an accurate alignment of the first body and second body, not only laterally across the motion segment, but also longitudinally (i.e. in the anterior/posterior direction) by virtue of the engagement of the keel and keel-ways.

It should also be noted that where a single body prosthesis (i.e. a single body prosthesis having only two members) is used, then there may be only one threaded recess and one shaped keyhole. Indeed, such a prosthesis may be inserted from the front of the spine, not from the back because of the obstruction caused by the spinal cord, and therefore the threaded recess and keyhole may be included on the anterior of the prosthesis; where anterior is relative to the spine.

Notably, in the preferred embodiment, the first body 10 and the second body 14 are inserted to the spine with the first body first member posterior portion 70 flush with the first body second member posterior portion 60, and similarly the second body first member posterior portion 72 is flush with the second body second member posterior portion 62. In such an arrangement the tapering of the first body first member vertebra contacting portion 18 and the first body second member vertebra containing portion 20 (likewise for the second body) can be accurately predetermined to match the intervertebral wedge angle of the appropriate motion segment to expedite insertion of the prosthesis.

The preferred embodiment of a four-piece prosthesis intended for posterior insertion shown in the figures also includes motion restraint means that limits the extent of motion of the first member relative to the second member, in a similar way to that provided by a facet joint. Thus, this embodiment is well suited to posterior insertion, a procedure that will often involve a laminectomy and/or facetectomy, which remove the facet joints. However, it should be noted that the substantially elliptical curves formed in the first and second member bearing surfaces are not an essential feature of a four-piece construction laterally spaced articulating intervertebral disc prosthesis having motion restraint.

Figure 5:
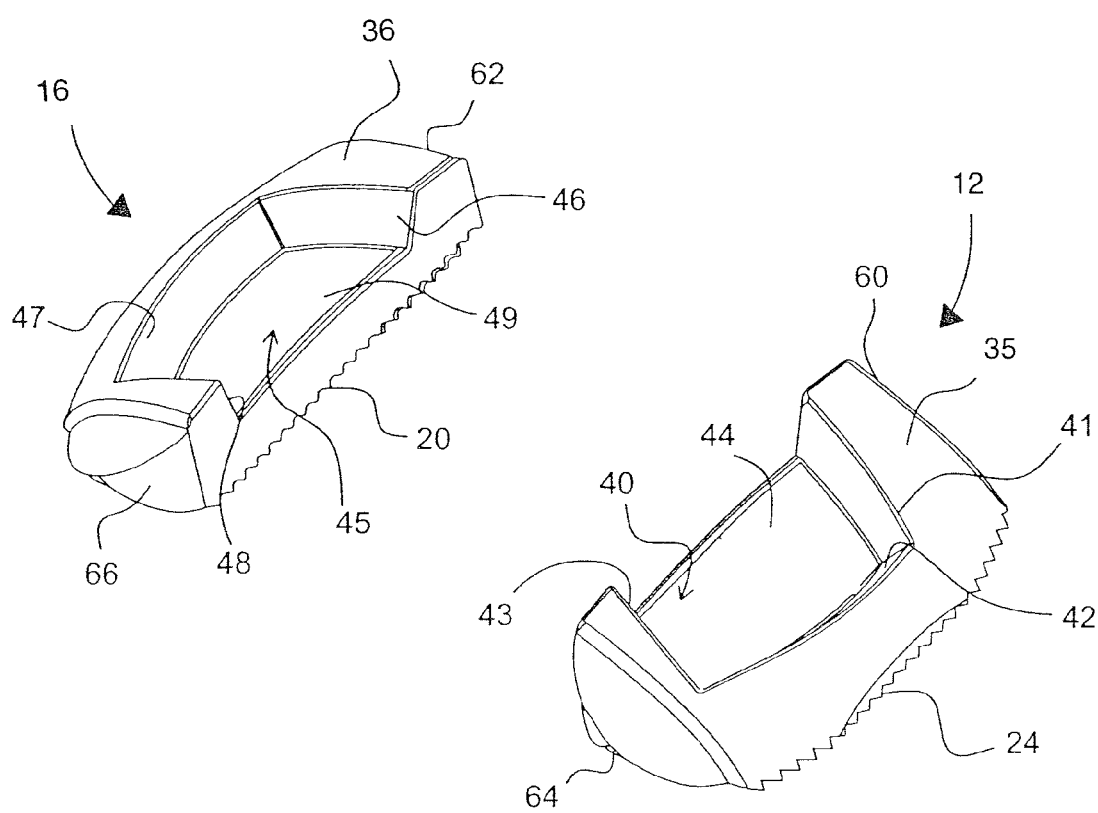
FIG. 5 is an oblique anterior view of a pair of members forming a part of a prosthesis, according to the present invention.

In the embodiment shown in FIG. 4 and FIG. 5, the motion restraint means is embodied by a recess or pocket 40 formed in the surface of the second member bearing surface 35 for receiving a finger 50 projecting from the first member bearing surface 30. Additionally, it is preferably that a prosthesis according to the present invention has a recess or pocket 45 formed in the surface of the second member bearing surface 36 for receiving a finger 55 projecting from the first member bearing surface 31.

The first member 11 and second member 12 forming the first body 10 have a finger 50 and a pocket 40 respectively, so arranged that articulation of the first member 11 about the second member 12 is restrained within predetermined limits. The first member 15 and second member 16 forming the second body 14 have a finger 55 and a pocket 45 respectively, so arranged to provide similar restraint.

Preferably, the pocket 40 and the finger 50 are arranged so that when the prosthesis is in place in the motion segment, the posterior face 51 of finger 50 abuts the posterior face 41 of the pocket or recess 40 when the motion segment is in the normal fully erect upright stance arrangement.

The preferred embodiment described here is intended for insertion through the posterior aspect of the spine. As such the prosthesis comprises two divided parts to allow avoidance of the obstruction caused by the spinal cord on insertion. However, an alternative embodiment (not shown) is envisaged where the first and second bodies are continuous, forming a single body where the two first members 11 and 15 have a continuous first member bearing surface formed at least in part from the first member bearing surfaces 30, 31; and the two second members 12 and 16 have a continuous second member bearing surface formed at least in part from the second member bearing surfaces 35, 36. Such a device would not be intended for insertion to the spinal column from the posterior aspect of the spine, and as such does not need to avoid the obstruction caused by the spinal cord. Such a two-piece construction (i.e. a single body, which includes two members) would, however, be suitable for anterior, lateral or transforaminal insertion.

Moreover, the insertion of such a two-piece device from the front would not necessarily require a laminectomy. Therefore, the facet joint can provide motion restraint in the motion segment, and so such an embodiment of the present invention may not require motion restraint means according to one or more of the aspects of the present invention.

However, another advantageous preferred feature of the preferred embodiment described here and shown in the figures is the orientation of the posterior wall 46 partly defining the recess 45 and the orientation of the posterior wall 41 partly defining the recess 40, which allow the coupling of the torsional rotation of the first and second members relative to each other when the finger 50 and 55 abut the posterior faces 41 and 46 of the pockets 40 and 45, i.e. at full extension of the prosthesis. This provides a prosthesis with ameliorated motion restraint, because, as previously described, the natural IVD and motion segment motion restraint permit coupling of certain ranges of motion, even at the limit of one of the ranges of motion.

Similarly, the anterior pocket walls are also preferably adapted to provide means for allowing the coupling of lateral translation and/or torsional rotation at a full extent of flexion of the prosthesis.

As mentioned above, when in a fully erect stance the finger abuts the posterior wall of the pocket. Therefore, the posterior walls 41 and 46 are angled such that when the device is in use in the intervertebral space, the walls are angled to the transverse axis, so that when the user is laterally bent over the posterior wall 41 permits the finger 50 to rotate. This permits the coupling of the lateral bending and the torsion of the vertebra 1 relative to the vertebra 2, as previously described. Preferably, the anterior walls of the pocket are arranged to also permit a degree of torsion at a maximum limit of flexion when rotating laterally.

Figure 6A:
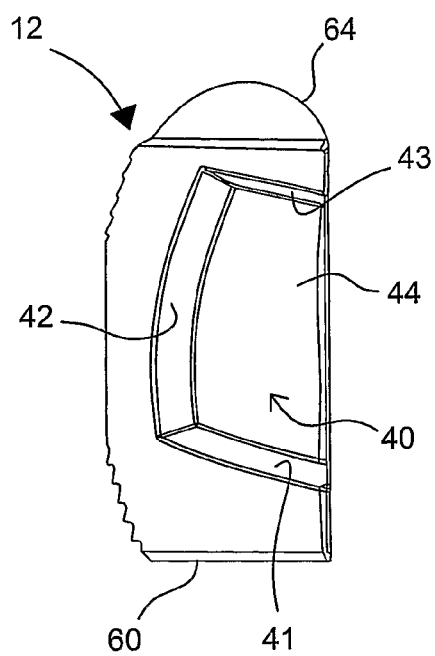
FIG. 6a is a plan view of a pair of members forming part of a prosthesis, according to the present invention, intended for use in the L3/L4 or L4/L5 motion segment, each member having a recess defined by walls arranged in a chevron configuration.
Figure 6A:
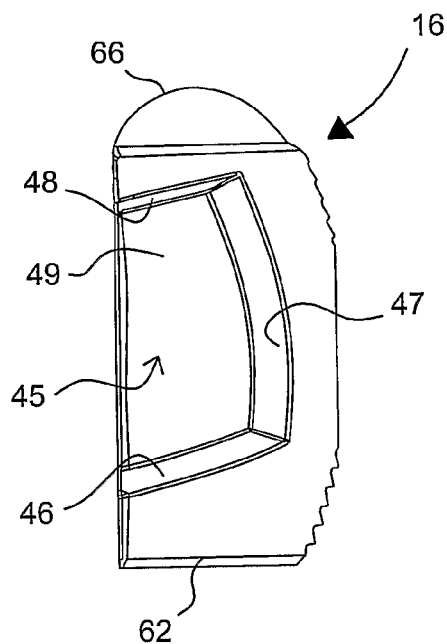

FIG. 6a shows a chevron configuration of the walls of the pockets 40 and 45 forming part of a prosthesis intended for use in a L3/L4 motion segment. This device is preferred for use in L3/L4 motion segment, where a user bending laterally to the user's left naturally creates a torque about the superior vertebra in the motion segment in the clockwise direction when viewed along the axis of the motion segment from the superior vertebra to the inferior vertebra, i.e. from above. The posterior walls 41 and 46 are angled so that when the prosthesis is in place in the spinal column the posterior wall is angled 13° from the transverse axis towards the anterior portion 64 and 66 respectively of the second members in a direction from the lateral extremes of each second member towards the mid point between the members.

Alternatively, the angle is 13° in a prostheses intended for use in a L4/L5 motion segment.

Preferably, the anterior walls 43 and 48 partly defining the pockets 40 and 45 are angled to the transverse axis by 3° towards the anterior portions 64 and 66 of the respective second members 12 and 16 in a direction from the lateral extremes of each second member towards the mid point between the members, in a prosthesis intended for use in both the L3/L4 and L4/L5 motion segments.

Figure 6B:
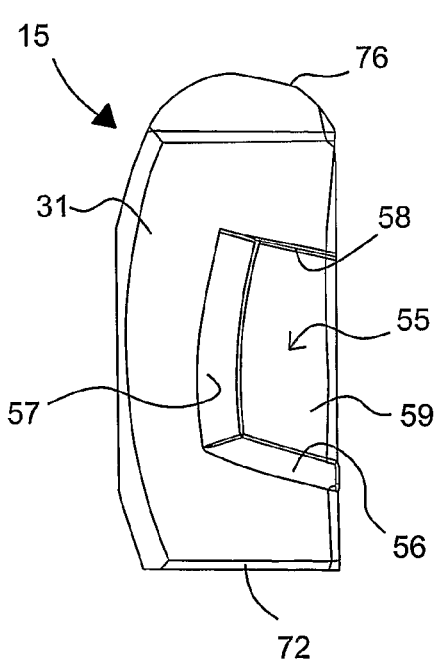
Figure 6B:
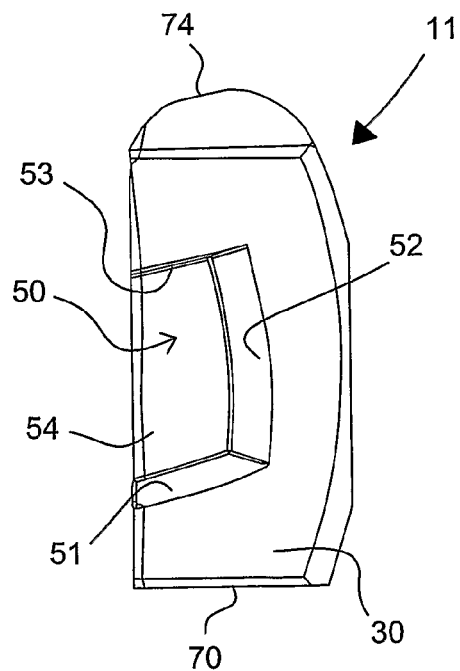

FIG. 6b shows a chevron configuration of the finger 50 and 55 forming part of a prosthesis intended for use in a L3/L4 motion segment. The posterior faces 51 and 56 of the fingers 50 and 55 respectively are angled to the transverse axis by 130 towards the anterior portions 74 and 76 of the respective first members 11 and 15. Preferably, the anterior faces 53 and 58 of the fingers 50 and 55 respectively are angled to the transverse axis by 3° towards the anterior portions 74 and 76.

Figure 7A:
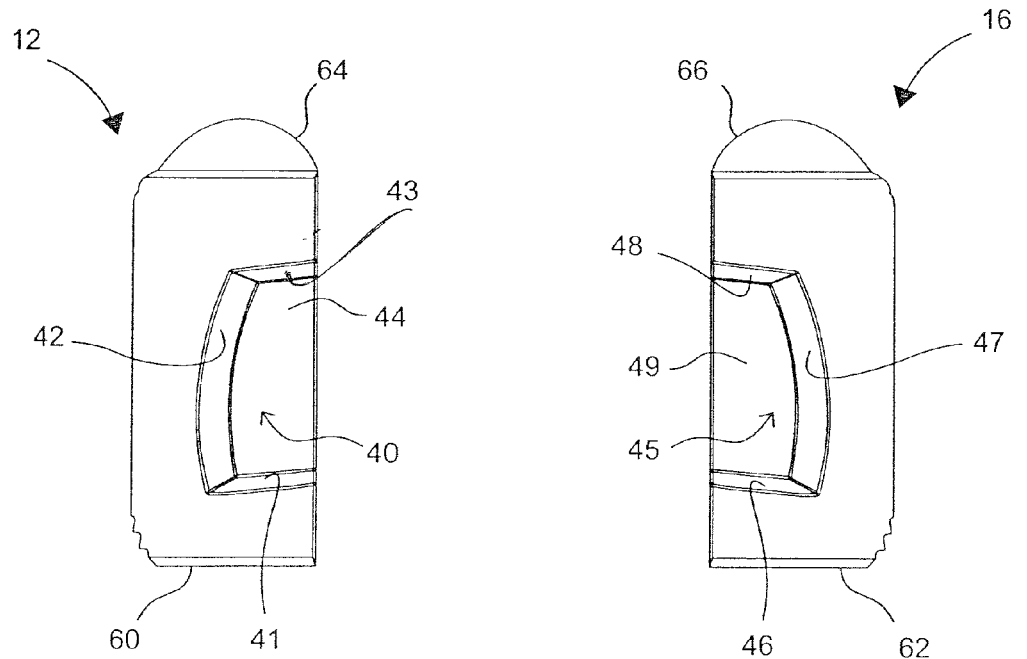
FIG. 7a is a plan view of a pair of members forming part of a prosthesis, according to the present invention, intended for use in the L5/S1 motion segment, each member having angled walls in an alternative chevron configuration, which define a recess.

FIG. 7a shows a chevron configuration of the walls of the pockets 40 and 45 forming part of a prosthesis intended for use in a L5/S1 motion segment. This device is preferred for use in the L5/S1 motion segments, where a user bending laterally to the user's left naturally creates a torque about the superior vertebra in the motion segment in the anti-clockwise direction when viewed along the axis of the motion segment from the superior vertebra to the inferior vertebra, i.e. from above. The posterior walls 41 and 46 are angled so that when the prosthesis is in place in the spinal column the posterior wall is angled 5° to the transverse axis towards the posterior portion 60 and 62 respectively of the second members. Preferably, the anterior walls 43 and 48 partly defining the pockets 40 and 45 are angled to the transverse axis by 10° towards the posterior portions 60 and 62 of the respective second members 12 and 16.

Figure 7B:
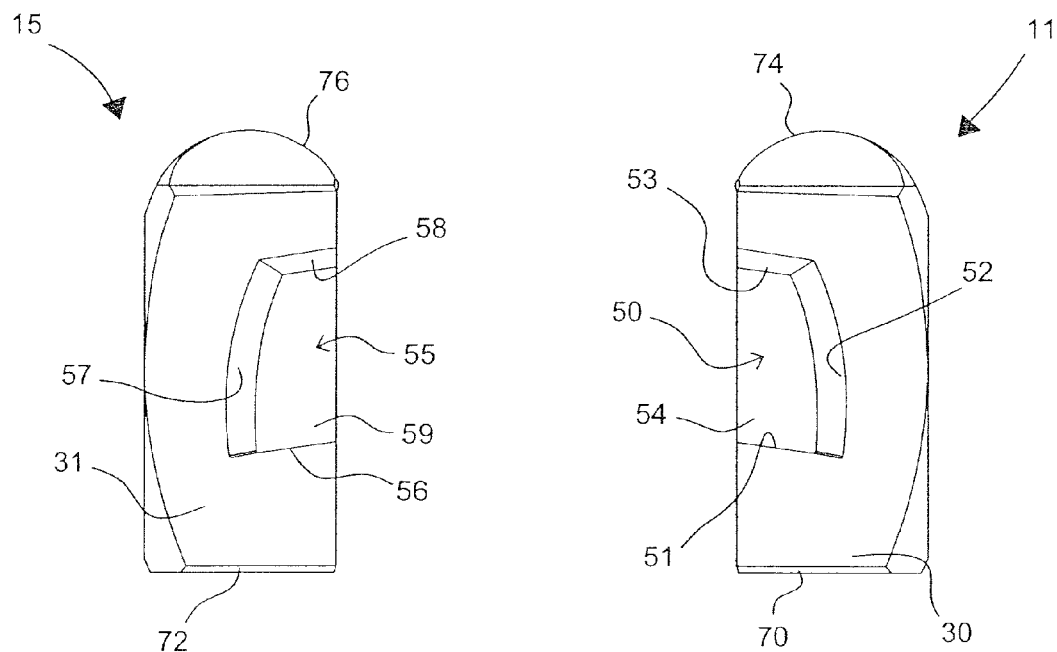

FIG. 7b shows a chevron configuration of the finger 50 and 55 forming part of a prosthesis intended for use in a L5/S1 motion segment. The posterior faces 51 and 56 of the fingers 50 and 55 respectively are angled to the transverse axis by 5° towards the posterior portions 70 and 72 of the respective first members 11 and 15. Preferably, the anterior faces 53 and 58 of the fingers 50 and 55 respectively are angled 10° towards the posterior portions 70 and 72.

Figure 8A:
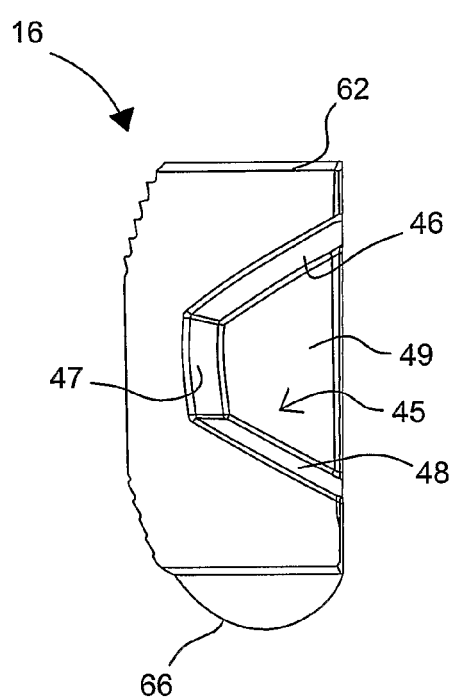
FIG. 8a is a plan view of a pair of members forming part of a prosthesis, according to the present invention, intended for use in the L3/L4 or L4/15 motion segment, each member having angled walls in a diamond configuration, which define a recess.
Figure 8A:
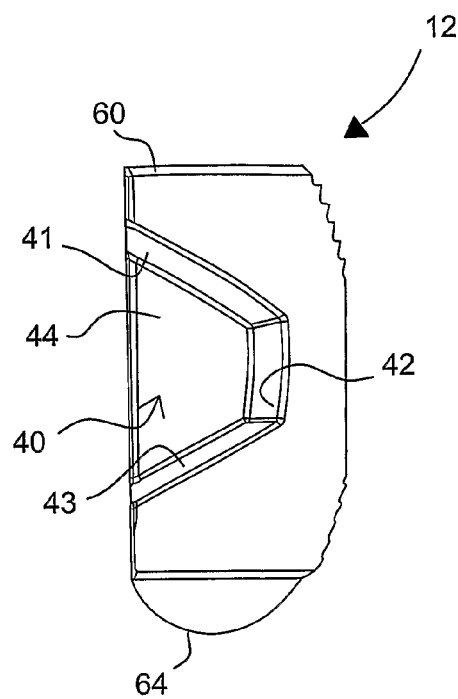

FIG. 8a shows a diamond configuration of the walls of the pockets 40 and 45 forming part of a prosthesis intended for use in a L3/L4 or a L4/L5 motion segment. The posterior walls 41 and 46 are angled so that when the prosthesis is in place in the spinal column the posterior wall is angled 30° from the transverse axis towards the anterior portion 64 and 66 respectively of the second members. Preferably, the anterior walls 43 and 48 partly defining the pockets 40 and 45 are angled to the transverse axis by 30° towards the posterior portions 60 and 62 of the respective second members 12 and 16.

Figure 8B:
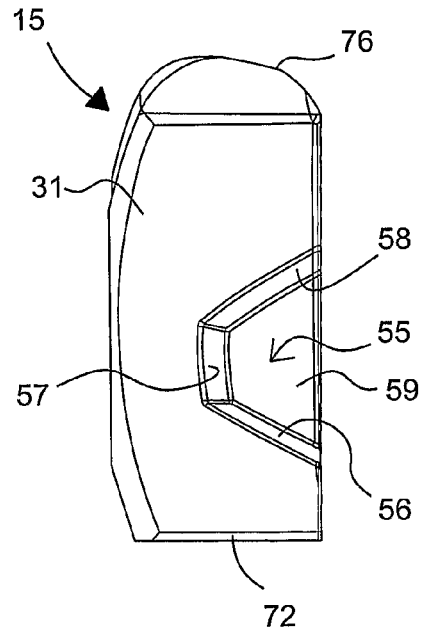
Figure 8B:
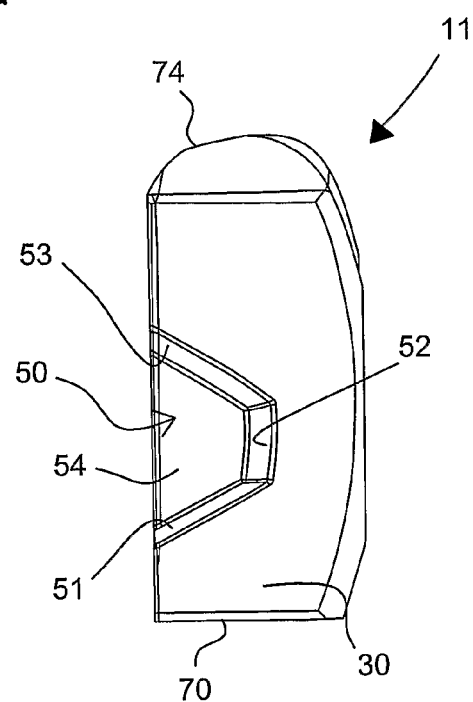

FIG. 8b shows a diamond configuration of the finger 50 and 55 forming part of a prosthesis intended for use in a L3/L4 or L4/L5 motion segment. The posterior faces 51 and 56 of the fingers 50 and 55 respectively are angled to the transverse axis by 30° towards the anterior portions 4 and 6 of the respective first members 11 and 15. Preferably, the anterior faces 53 and 58 of the fingers 50 and 55 respectively are angled 30° towards the posterior portions 70 and 72.

Figure 9A:
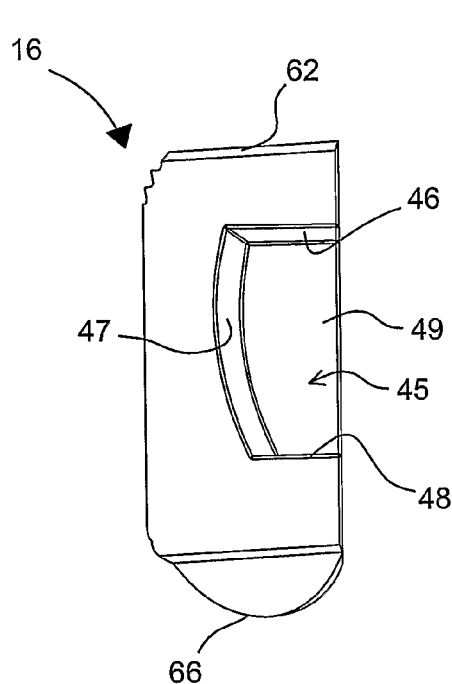
FIG. 9a is a plan view of a pair of members forming part of a prosthesis, according to the present invention, intended for use in the L5/S1 motion segment, each member having angled walls in a "dicky-bow" like configuration, which define a recess.
Figure 9A:
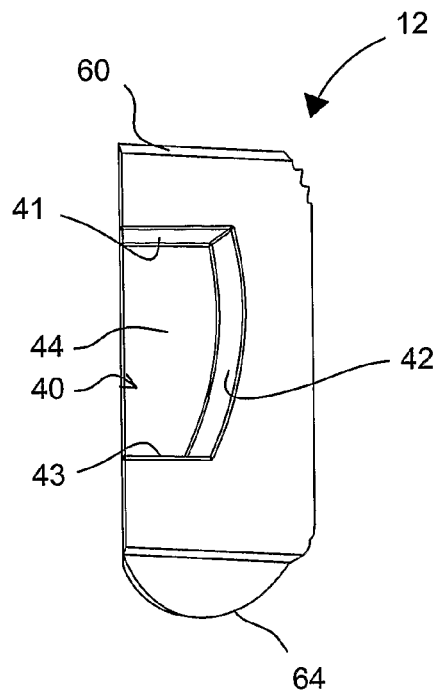

FIG. 9a shows a dicky-bow type configuration of the walls of the pockets 40 and 45 forming part of a prosthesis intended for use in a L5/S1 motion segment. The posterior walls 41 and 46 are angled so that when the prosthesis is in place in the spinal column the posterior wall is angled 520 from the transverse axis towards the posterior portion 60 and 62 respectively of the second members. Preferably, the anterior walls 43 and 48 partly defining the pockets 40 and 45 are angled to the transverse axis by 5° towards the anterior portions 64 and 66 of the respective second members 12 and 16.

Figure 9B:
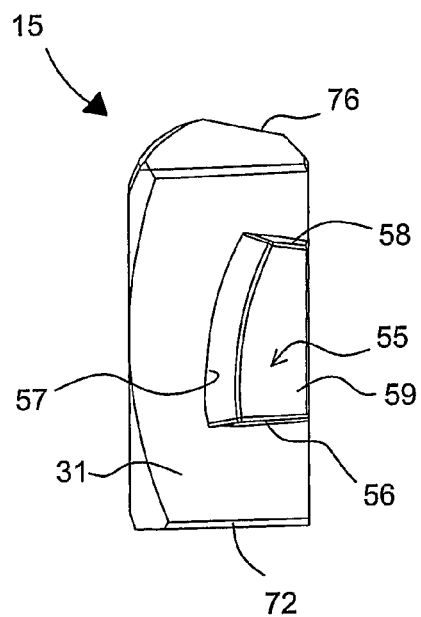
Figure 9B:
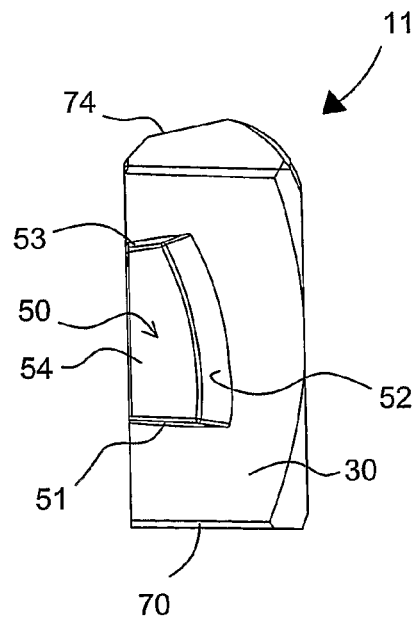

FIG. 9b shows a dicky-bow type configuration of the finger 50 and 55 forming part of a prosthesis intended for use in a L5/51 motion segment. The posterior faces 51 and 56 of the fingers 50 and 55 respectively are angled to the transverse axis by 5° towards the posterior portions 70 and 72 of the respective first members 11 and 15. Preferably, the anterior faces 53 and 58 of the fingers 50 and 55 respectively are angled 5° towards the anterior portions 74 and 76.

In the present embodiment, a preferred feature is shown in FIGS. 3a, 3b and 3c, that the end face 54 of the finger 50 abuts the recess floor 44. It is preferred that the recess floor 44 is formed to approximate to a portion of a spheroidal surface, e.g. an oblate spheroid.

Preferably, the end face 54 of the finger 50 is also formed to approximate to a portion of a spheroidal surface, e.g. an oblate spheroid.

Another articulating intervertebral disc prosthesis according to the present invention includes a first member having a vertebra engaging portion, which engages in use a first vertebra, and a bearing surface; a second member having a vertebra engaging portion, which engages in use a second vertebra, and a bearing surface, which abuts the first member bearing surface to form an articulating first bearing joint; and motion restraint means adapted to provide articulation restraint of the first bearing joint at pre-determined limits of articulation; wherein the motion restraint means includes first and second elements which are part of the first and second members respectively and those elements co-operate throughout the range of articulation of the first bearing joint to form a second articulating bearing joint; and wherein the second member bearing surface of each first and second articulating bearing joint is shaped to include at least a portion of a first circular curve when viewed in use in a first section parallel to the sagittal plane, at least a portion of a second circular curve when viewed in use in a second section parallel to the coronal plane, and at least a portion of a third circular curve when viewed in use in a third section parallel to the transverse plane, said first, second and third curves being of respectively different sizes of circle such that the second member bearing surface is aspherical.

In the most preferred embodiment, the axes of rotation of each of the spheroidal surfaces of which the first member bearing surface 30, of which the second member bearing surface 35, of which the end face 54 of the finger 50, and of which the recess floor 44 are portions, can be coincident. These preferred features can equally be applied to the second body, but has not been explicitly described here to avoid repetition.

The preferred feature, described above, produces an increase in the bearing surface area in the prosthesis, thereby spreading the load over a larger area and potentially reducing localised wear.

Figure 10:
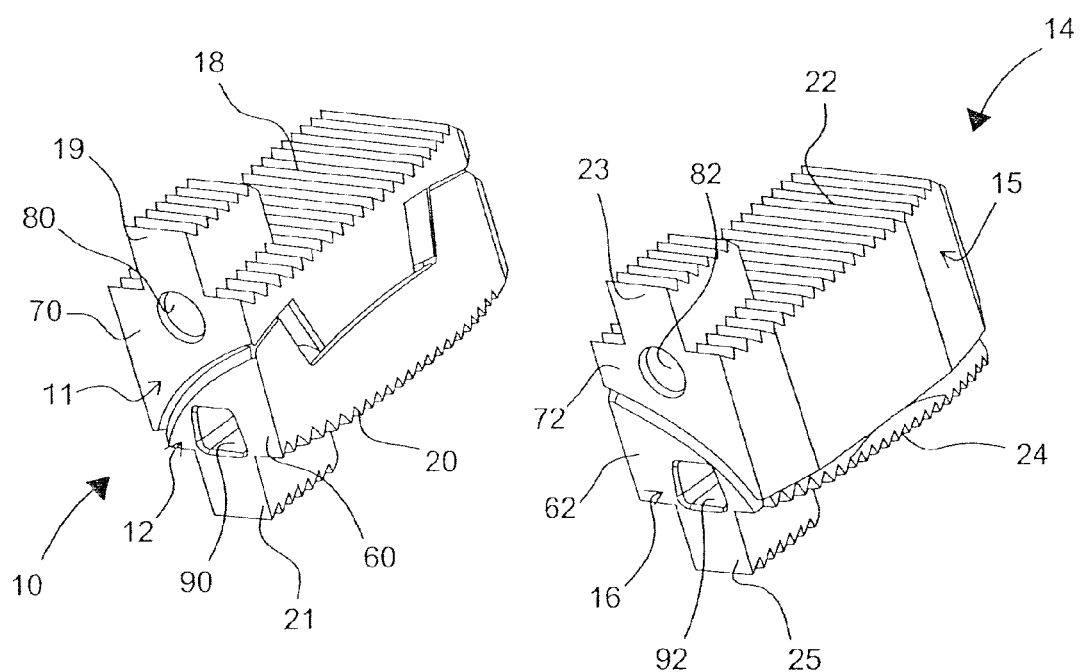
FIG. 10 shows a posterior oblique view of an embodiment of the present invention.
Figure 11A:
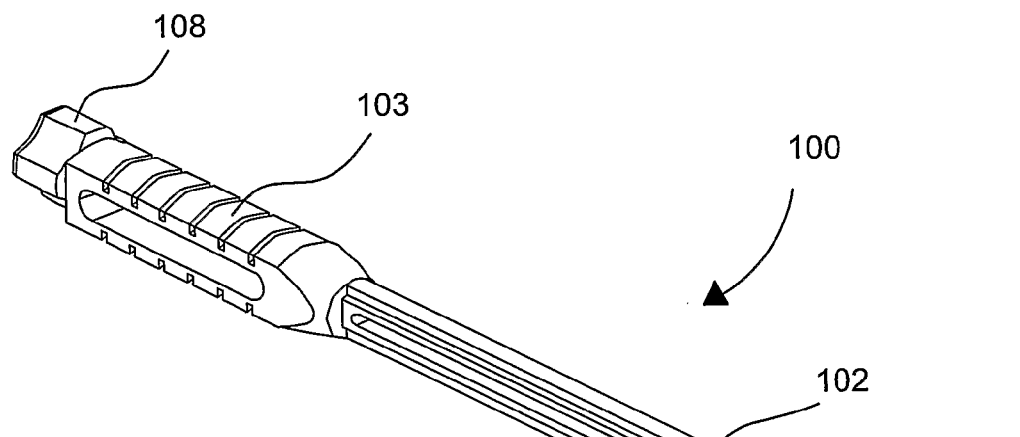
FIG. 11a shows a prosthesis implant instrument according to the present invention.
Figure 11B:
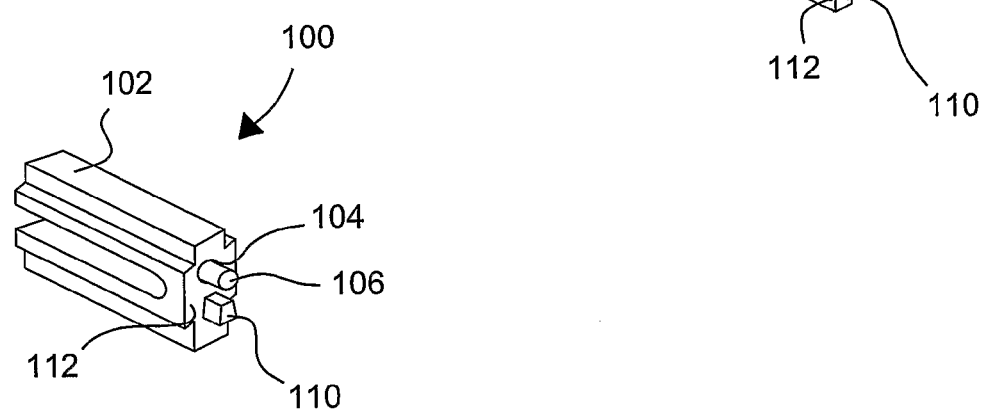
FIG. 11b is a view of the end of the instrument of FIG. 11a, for engagement with a prosthesis, according to the present invention.
Figure 11C:
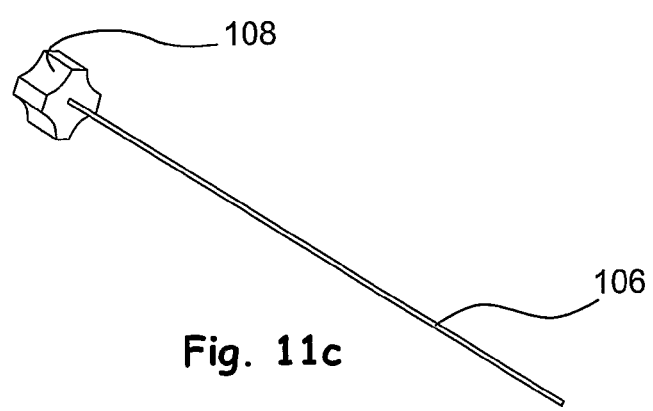

FIG. 10 shows another embodiment of the present invention. In the figure each body of the prosthesis is arranged in the insertion position, i.e. with the posterior faces 70 and 60 of the first body first and second members 11, 12 respectively, flush. The second body is similarly so arranged. In this arrangement, the insertion instrument or tool 100 shown in FIG. 11a, can be engaged with each of the first body 10 and second body 12 in turn.

The preferred insertion instrument 100 shown in the figures has an elongated shaft 102 which defines a passage 104 along its length, there being a passage aperture defined at both ends of the shaft 102. At one end of the instrument 100, for example one end of the shaft 102, there is a handle 103 which has a passage (not shown) co-axial with the passage 104 in the shaft 102. A threaded spindle 106 is rotatable in the passage 104, and in the passage (not shown) in the handle 103. Preferably, the rotatable spindle 106 is capable of sliding axially along the passage 106. At one end of the spindle 106 it is preferred that the spindle includes means 108 for rotating the spindle; such means could be a flange for example. Preferably, the means 108 are so arranged that the means 108 abuts the handle 103 when the spindle 106 is located in the passage 104, and the spindle 106 is at its fullest insertion in the passage 104.

Crucially, a portion of the threaded spindle 106 protrudes through the opening of the passage 104 at the end of the shaft 102 distal to the handle 103. Preferably, the protrusion of the spindle is a projection sufficient to engage with a complementary threaded recess when the means 108 abuts the handle 103.

Adjacent the opening of the passage 104, through which the spindle 106 protrudes, there is formed a key 110. Preferably, this key 110 is shaped to have only one degree of rotational symmetry. In this preferred embodiment, the key 110 is shaped to be a trapezium, but can be square, rectangular or triangular when viewed parallel to the long axis of the shaft 102.

In use, the key 110 is received by the keyhole 90 (or 92) of the first body 10 (or the second body 14) of the preferred embodiment of a prosthesis according to the present invention. The particular symmetry of the key 110 and complementary keyhole 90, 92 is such that the second member 12 (or 16) can only be mounted to the instrument 100 in one orientation. In this preferred embodiment, that orientation is such that the bearing surface of the second member is proximal to the spindle 106, preferably the posterior portion 60 (or 62) of the second member abuts the shaft end 112, and at least a portion thereof is preferably continuous with a portion of the shaft end 112.

Furthermore, the first member 11 (or 15) which is disposed in abutment with the second member 12 (or 16) so that the respective bearing surfaces are contacting, is engaged with the spindle 106 by screwing the spindle 106 into the complementary threaded recess 80 (or 82).

Preferably, because the means 108 abuts the handle, as the spindle is rotated, the first member is drawn along the axis of the shaft until the posterior portion 70 (or 72) of the first member 11 (or 15) abuts the shaft end 112. Preferably, at least a portion of the posterior portion 70 (or 72) is contiguous with a portion of the shaft end 112.

Figure 12:
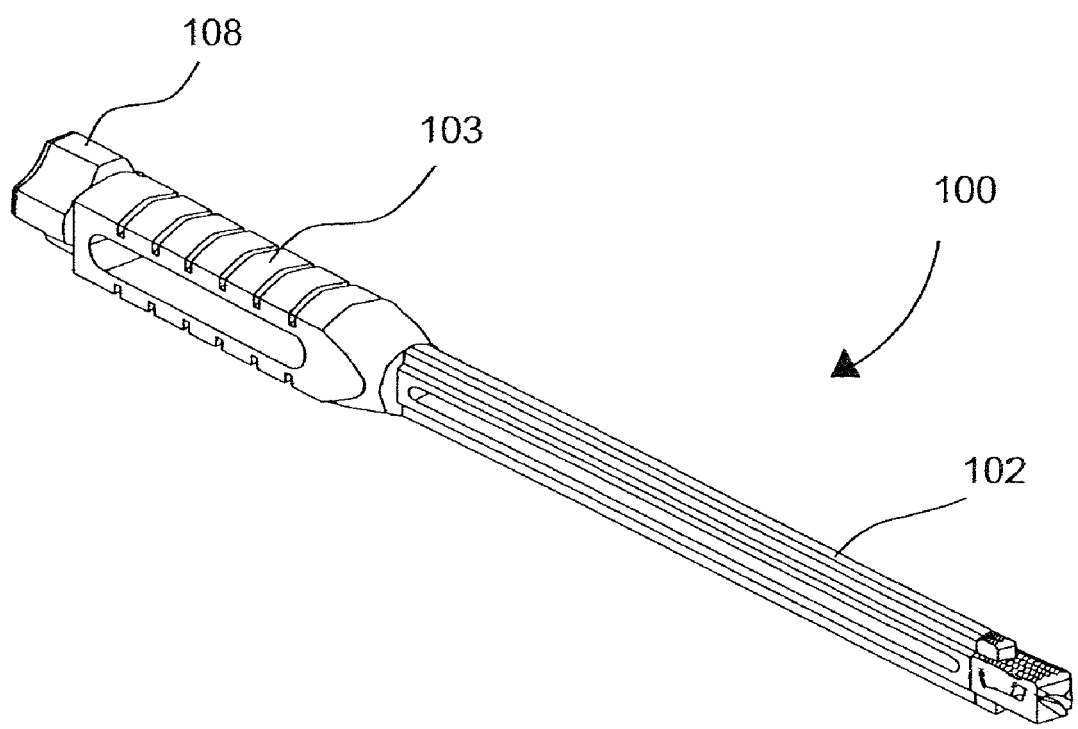

The first body 10 or second body 14 is thus held rigidly by the instrument 100 and is prevented from articulating, as is shown in FIG. 12. Once the body has been inserted to the IVD space, the spindle 106 can be counter-rotated to release the first member 11 (or 15) and the key 110 can be disengaged from the keyhole 90 (or 92).

Figure 13:
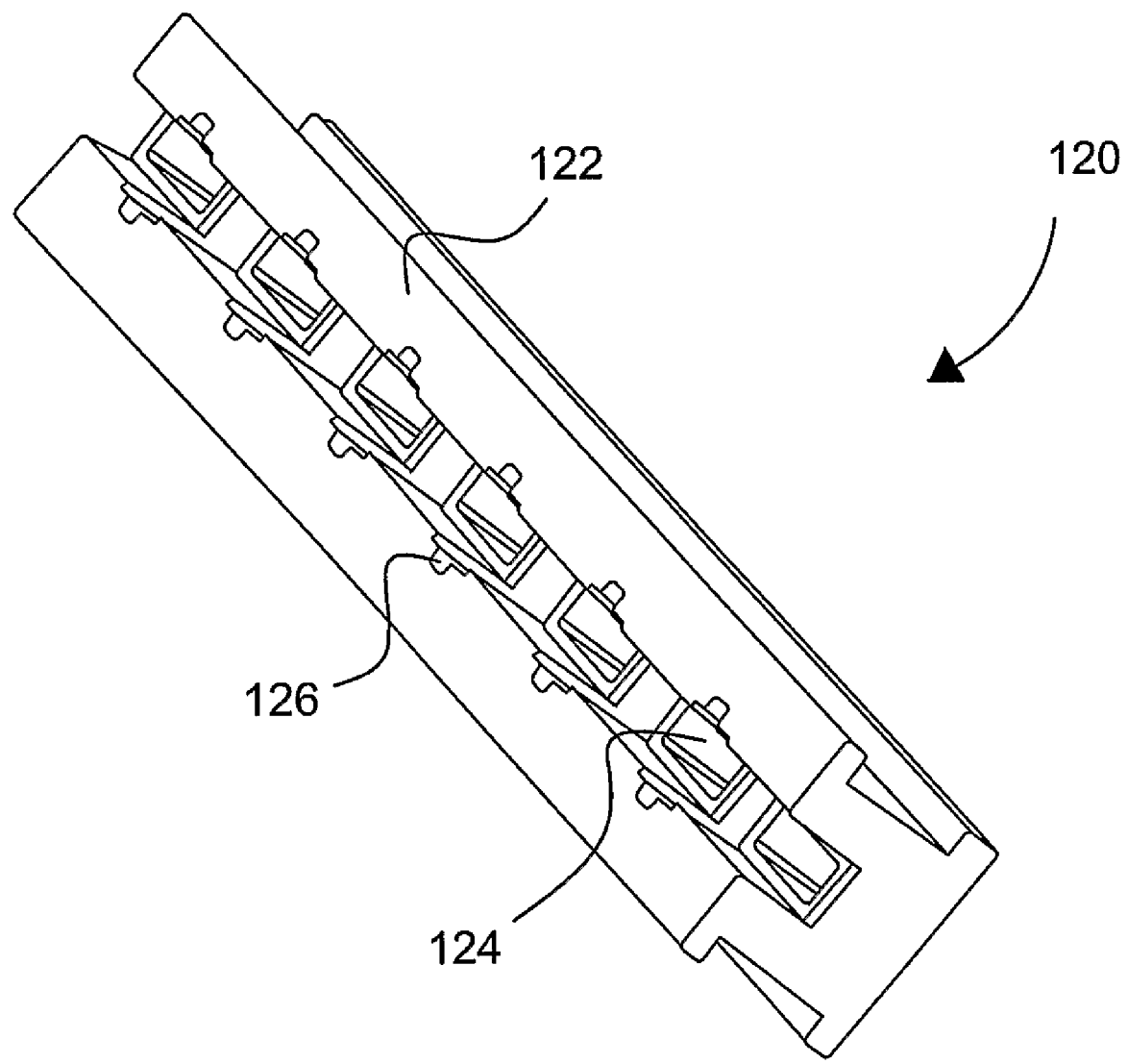
FIG. 13 is a view of a cartridge for holding a number of prostheses according to the present invention.

FIG. 13 shows a preferred embodiment of a cartridge 120 for housing a plurality of first and/or second bodies 10, 14. The preferred cartridge has a housing 112 in which is formed one or more bays 124 for receiving a first body 10 or a second body 14. Along the axial direction of each of the bays 124, there are formed docking or storage keel-ways 126, each for receiving one of the keels 19, 21, 23, 25 of the first or second bodies. Preferably, the posterior portions of the first and second members are preferably made flush when inserted to the bay 124.

Figure 14:
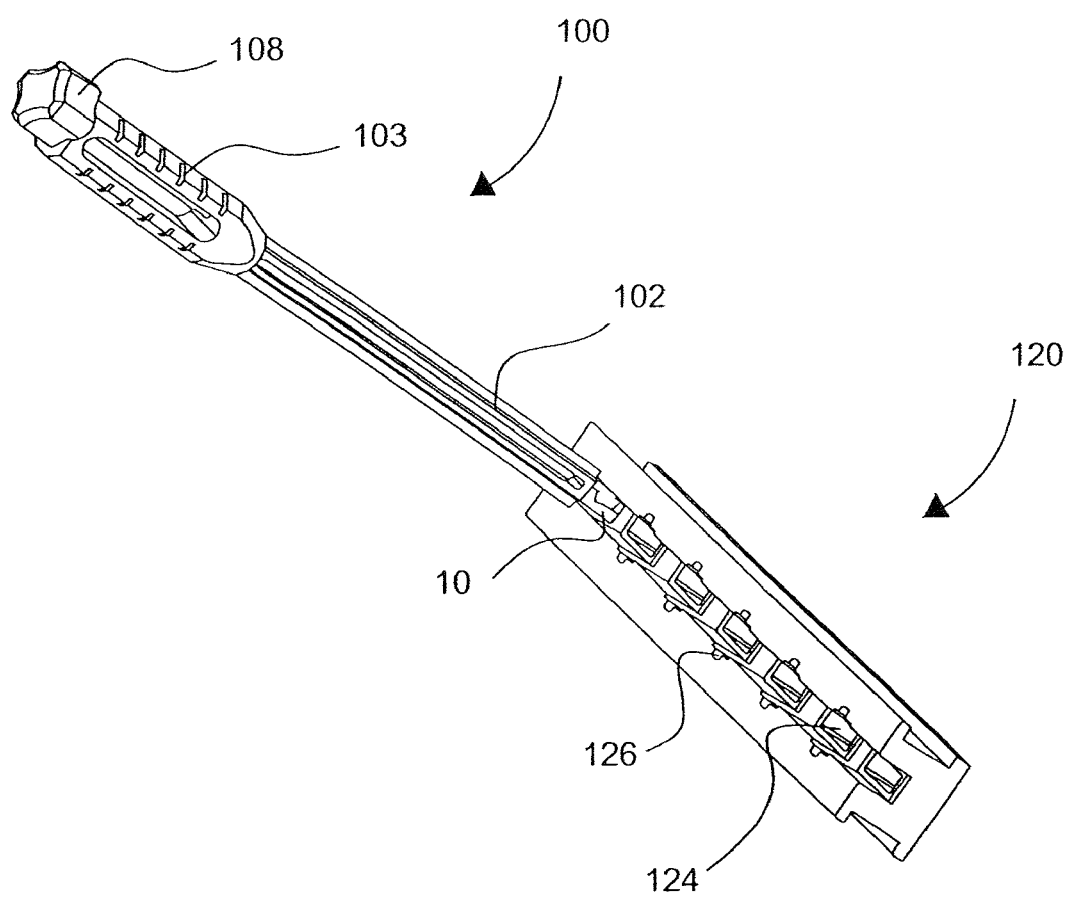
FIG. 14 shows the implant instrument of FIG. 11a engaged with a prosthesis located in the cartridge of FIG. 13, according to the present invention.

This is preferred because the body is then in the same arrangement that it is when fully mounted on, and engaged with, the insertion instrument 100, and so expedites the procedure of mounting the prosthesis body onto the instrument, as shown in FIG. 14.

Importantly, both the cartridge 120 and the insertion instrument 100 align the keels 19, 21 (or 23, 25) of the first body 10 (or the second body 14). This is advantageous for insertion, because accurate alignment of the keels to the pre-defined keel-ways speeds up the implantation procedure.

Figure 15:
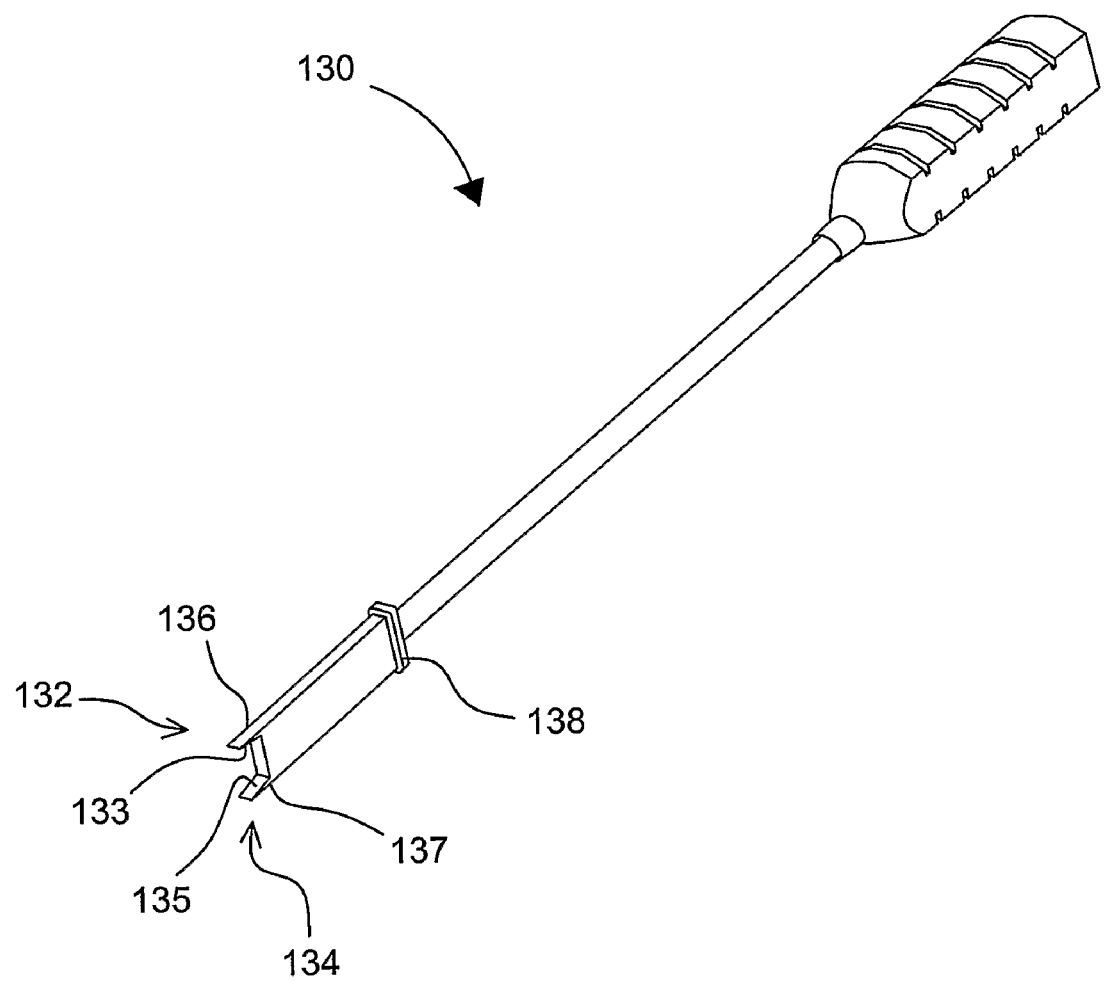
FIG. 15 is a view of a chisel, according to the present invention, for forming a channel in vertebrae.

The keel-ways in the first and second vertebrae can be formed by chiselling away portions of the respective vertebra. However, because the keel-way in the first vertebra 1 must be accurately aligned with the keel-way in the second vertebra 2 it is preferred that the pair of keel-ways is formed with the same chisel, preferably contemporaneously. To achieve this, FIG. 15 shows a chisel designed to form a pair of opposing keel-ways contemporaneously, one in each of the first and second vertebra.

The chisel 130 has at one end a pair of prongs or tines 132 and 134. The prong 132 has an angled face 133, and the prong 134 has an angled face 135. The angled faces face one another across the broad width of the chisel, and are angled to the long axis of the chisel. The angled faces 133 and 135 are angled to diverge along the axis of the chisel in the direction of use of the chisel. At the end of the prongs, the divergence of the faces 133 and 135 creates two blade edges. The angled face 133 meets a face 136 that is substantially parallel to the long-axis of the chisel 130. The angled face 135 meets a face 137 that is substantially parallel to the long-axis of the chisel 130.

The two blade edges are preferably parallel, and in use, the chisel is impacted to the vertebra to create a first channel in the first vertebra, and a second channel in the second vertebra. The first and second channels are thus formed in direct spatial opposition.

Figure 16:
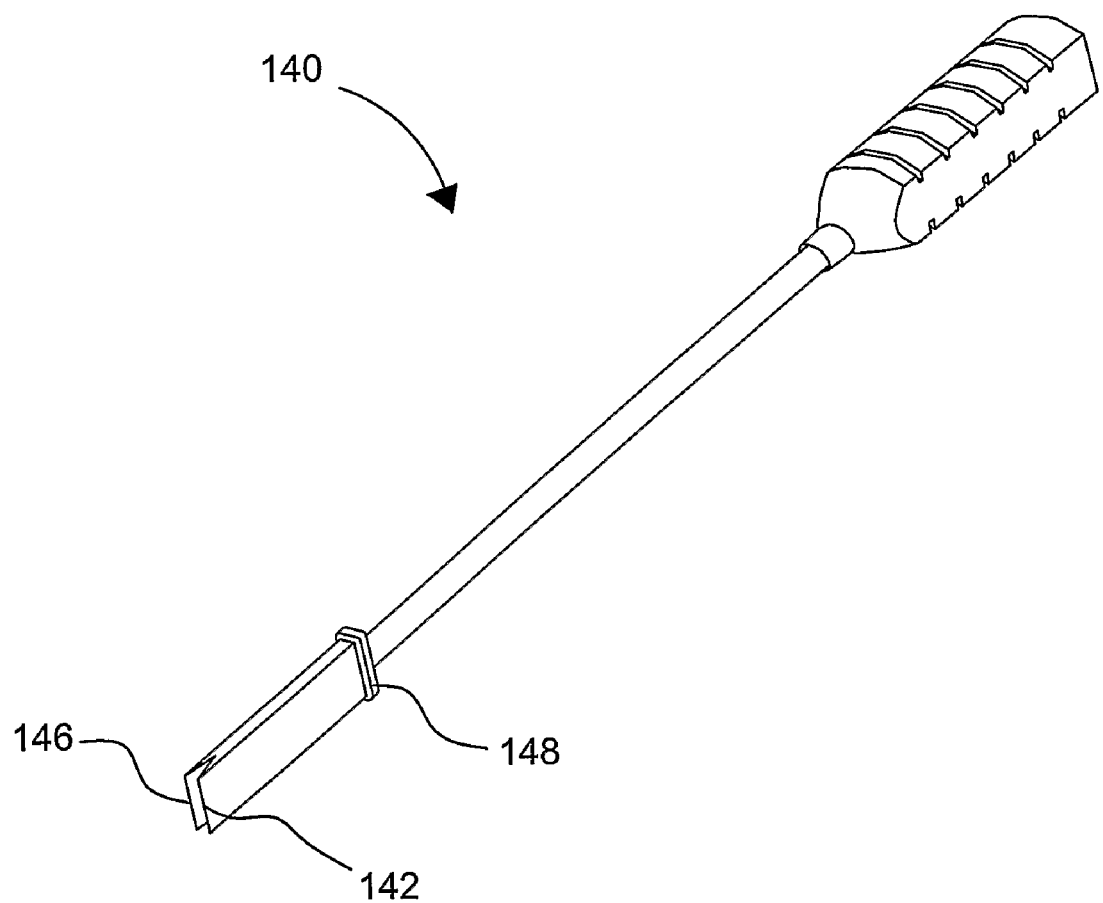
FIG. 16 is a view of another chisel, according to the present invention, for forming a channel in vertebrae.

The two blade edges create a smooth and clean floor to the lower channel, and a smooth and clean ceiling to the upper channel. FIG. 16 shows a chisel 140 for making the side walls of both channels smooth and clean, and for making the four sides (i.e. two side walls in the upper channel, and two side walls in the lower channel) parallel. A second chisel 140 is formed to have two parallel blades 142 and 146 along the broad width of the tip of the chisel, the blades are spatially separated to a predetermined width. This predetermined width is preferably slightly less than the width of the keel intended to be inserted to the channel or keel-way.

The chisel 140, when driven into the channels pre-formed by the chisel 130, effectively makes both side walls of both the channel in the first vertebra and the channel in the second vertebra planar and parallel, contemporaneously.

An alternative chisel (not shown) is a box chisel formed by combining the chisel 140 and 130, so that all the walls, parallel to the direction of action of the chisel, of a channel formed contemporaneously in both the first and second vertebrae are made to have smooth and planar walls when the chisel is used.

Although the above-described chisels can form a channel in the first and second vertebra contemporaneously, and in direct spatial opposition, it is clear that the two, or more, keel-ways formed in the first vertebra 1 (or the second vertebra 2) for receiving the keels 19 and 23 must be very accurately aligned and must be spaced apart accurately and with precision. This is particularly true for the preferred embodiment shown in FIG. 3a, where the co-operation of the bearing joint in the first body 10 and the second body 14 relies on the first body 10 and the second body 14 being accurately spaced apart, so that the centre(s) of articulation of the first body bearing joint and the second body bearing joint is/are coincident. Particularly, in this preferred embodiment, the second member bearing surfaces 35 and 36 may be formed to approximate to portions of the same spheroidal surface, e.g. an oblate spheroid, and so it is important that the centre of rotation of the two portions are coincident if the two bearing joints are to co-operate effectively and efficiently. This is similarly true of the bearing surfaces 30 and 31 of the first and second body first members 11 and 15.

Figure 19A:
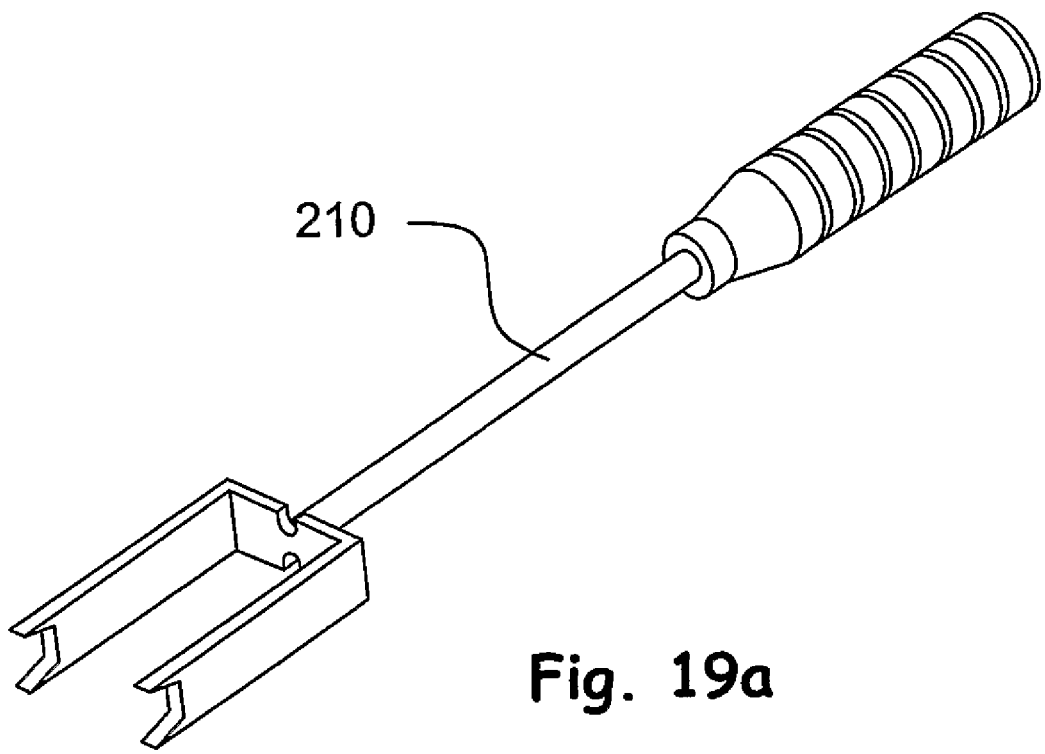
FIGS. 19a and 19b show alternative embodiments of chisels according to the present invention.
Figure 19B:
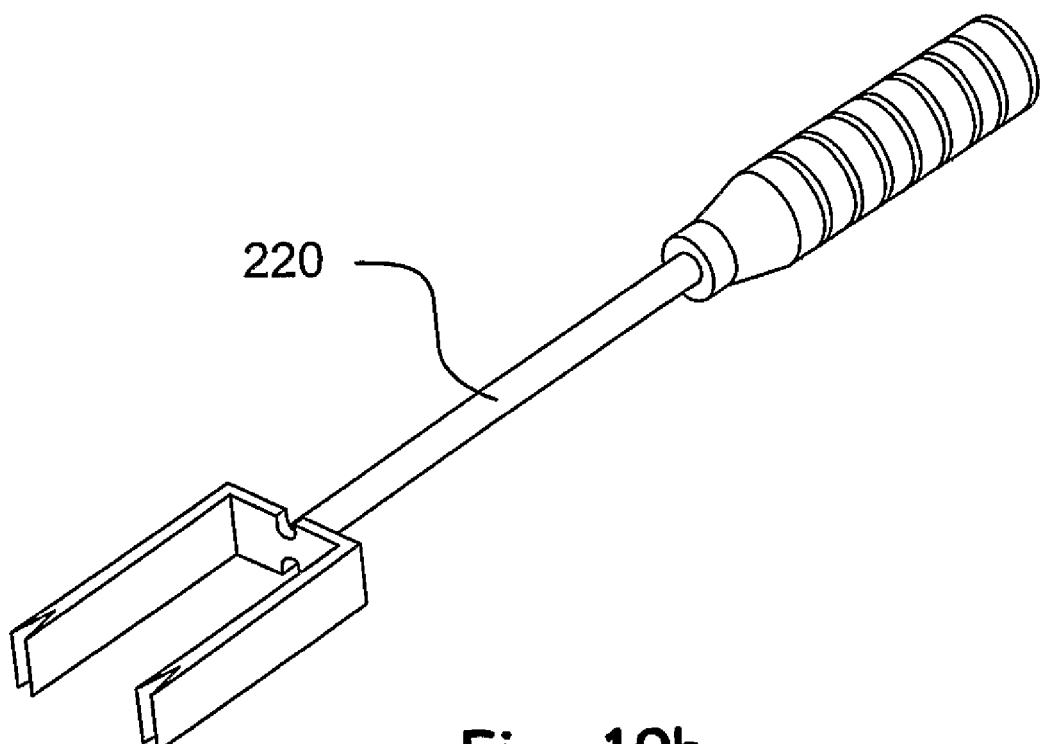

One way of ensuring that the keel-ways are formed accurately could be to use a single chisel which cuts both keel-ways (or parts of both keel-ways) simultaneously. FIGS. 19a and 19b show a pair of chisels 210 and 220 for this purpose. FIG. 19a shows a bilateral keel-way chisel for forming the inferior/superior cut and FIG. 19b shows a bilateral keel-way chisel 220 for forming the medial/lateral cut. As will be apparent, each bilateral chisel essentially consists of a pair of chisels as shown in FIGS. 15 and 16 respectively.

Figure 17:
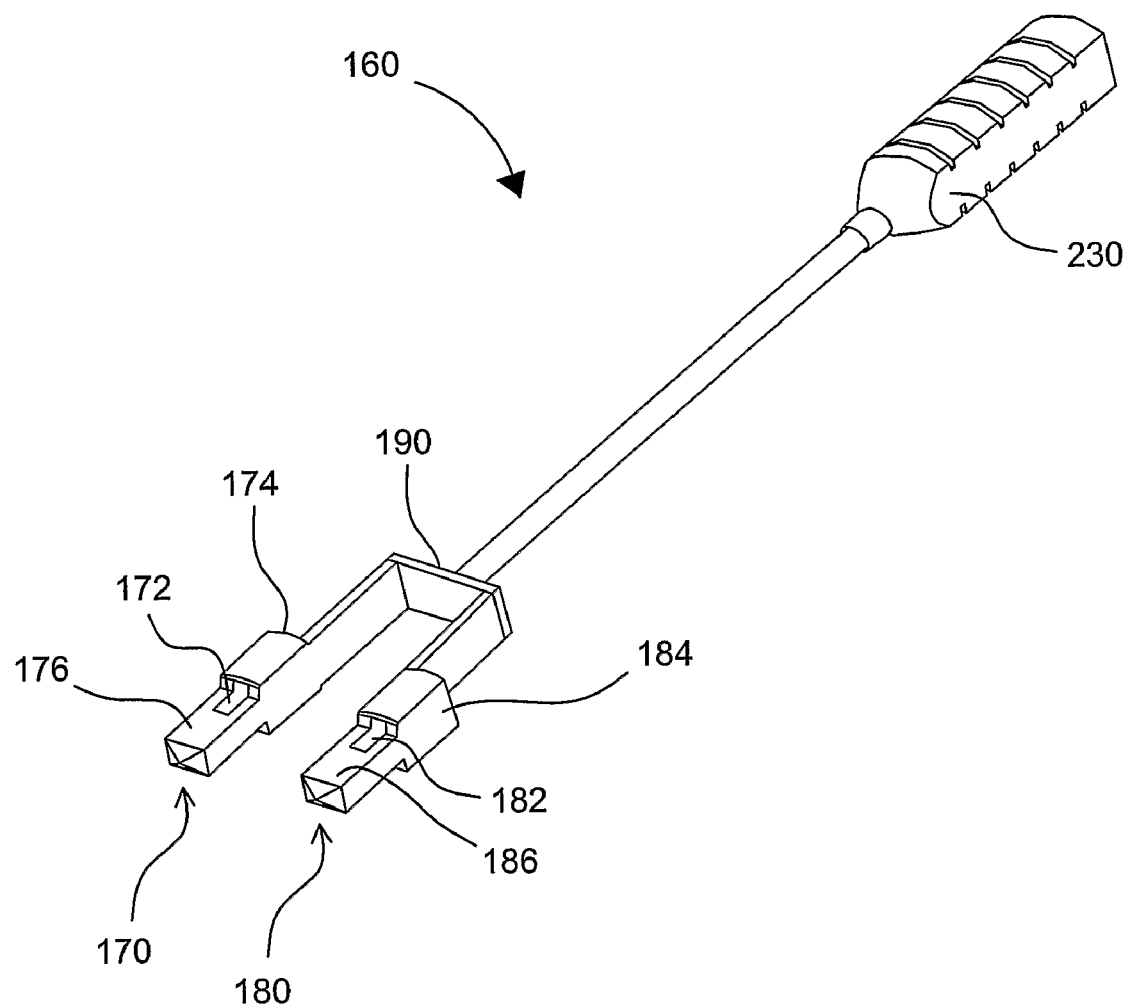
FIG. 17 is a view of a guide-instrument, according to the present invention, that provides a means of accurately forming the chiselled channels in vertebrae.

Alternatively, to ensure that the keel-ways are formed accurately in the vertebrae to the correct spatial separation, i.e. that the keel-ways formed in the first vertebra are accurately laterally spaced apart to a predetermined extent, a chisel alignment tool 160 is provided as shown in FIG. 17. The alignment instrument 160 includes at least two chisel guide-ways 170, 180. The guide-ways 170, 180 each define a chisel passageway 172 and 182 into which one of the chisels 130, 140 (or the box chisel) can be inserted through the guide aperture 174 to the passageway 172, or through the guide aperture 184 to the passageway 182.

The end of each guide-way 170, 180 distal to the respective guide aperture 174, 184 is adapted so that the respective passageway 172, 182 is exposed. This exposure means that when a chisel (e.g. chisel 130) is slid axially along the guide-way, a portion of the chisel protrudes from the passageway in the region of adaptation of the guide-way.

In this preferred embodiment a portion of each guideway is cut away to form a step-like structure at the end of the guideway distal to the respective guide aperture 174, 184. The narrow step portion 176, 186 can then be inserted between the adjacent vertebra and act as a spacer member to hold apart the vertebra as a chisel is slid axially along one or both of the guide-ways 170, 180.

So that the keel-ways can be formed in the adjacent vertebra contemporaneously, the guide-ways 170, 180 are formed to have a cut-away portion on opposite sides of each guide-way, thereby to expose from the respective passageway 172, 182 a portion of the chisel to both the adjacent vertebra, one on either side of the step-like portion of the guide-way.

In a more preferred embodiment, a portion of the said guide-way is cut away to form a step-like structure more proximal to the respective guide apertures 174, 184. This more proximal step-like structure is designed to abut the pars interarticularis, once the chisel alignment tool 160 is properly located for use For the avoidance of doubt, it is hereby stated that the cut-away portion need not be formed by literally cutting away a portion of the guide-way. The guide-way may be formed by any means known in the art, for example by moulding, by forging, or in any other way.

The most important feature of the alignment tool is the cross-beam 190 that fixes the separation of the guide-ways 170, 180 to a predetermined extent. Although the separation of the guide-ways 170, 180 by the cross-beam 190 is predetermined, it is possible that the cross beam 190 could be adapted so that the separation between the guide-ways 170 and 180 is variable, between 15-30 mm but preferably it is fixed, and most preferably it is fixed to 24 mm. It is merely a requirement that the cross-beam 190 fixes the separation rigidly, so that that when performing the operation to form the keel-ways, the separation between the guideways 170 and 180 is not altered.

The cross-beam 190 fixes the lateral separation of the passageways 172 and 182 and therefore when the instrument 160 is inserted between the adjacent vertebrae of a motion segment, the keel-ways are formed at the predetermined separation of the passageways fixed by the cross-beam 190.

Preferably, the cross-beam 190 also serves as abutment means to act as a motion stop for the chisel as it slides axially along one of the guide-ways 170 and/or 180. This is effected by the chisels 130, 140 preferably including, respectively, a flange 138, 148 projecting substantially laterally from the axis of the chisel to engage with the cross-beam 190. This cross-beam 190 is identified to provide the motion stop means for the bilateral keel-way chisels 210 and 220. In this embodiment, the alignment tool handle 230 would be detachable from the main body of the instrument. Alternatively, another part of the guide-ways 170, 180 may serve as abutment means for limiting the motion of the chisel, for example the part of each guide-way that defines the aperture 174 and 184 to which the chisel is inserted.

Figure 18:
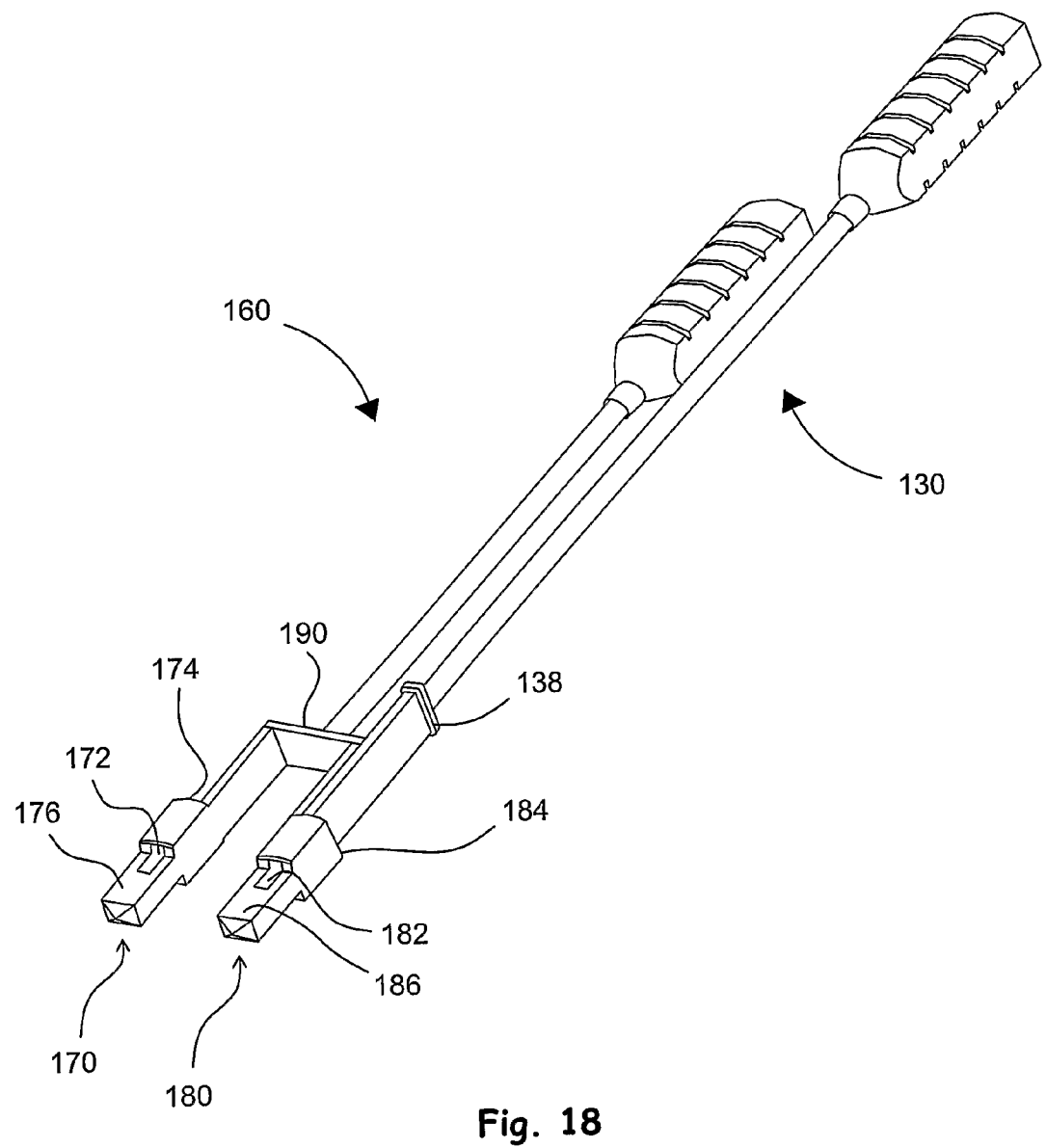
FIG. 18 shows a chisel mounted in one of the guide-ways of the guide-instrument of FIG. 17, according to the present invention.

FIG. 18 shows the alignment instrument 160 in a state of readiness for use, in which the chisel 130 is partially inserted to the guide-way 180 to extend part way down the passageway 182.

In an alternative embodiment, the chisel 130 is connected by a cross-bar to another chisel located in the guide-way 170 to extend at least partly along the passageway 172.

In accordance with the present invention, different sizes of prosthesis may be provided, i.e. relatively small prosthesis for use in the spine of a child, or relatively larger prosthesis for use in the spine of an adult. Thus, the alignment tool shown in FIGS. 17 and 18 would preferably be adjustable so that the separation between the guide-ways 170 and 180 can be adjusted to match the critical separation of the keel-ways of the first body and second body of a four-piece laterally spaced prosthesis, e.g. as shown in FIG. 3a.

In an alternative embodiment (not shown) in which the second member bearing surfaces 35, 36 are shaped to be, or formed to approximate to, a portion of an ellipsoidal surface, the ellipsoidal surface has a principal axis parallel to the transverse axis (see FIG. 2a) when the prosthesis is in place in the intervertebral space.

Figure 1:
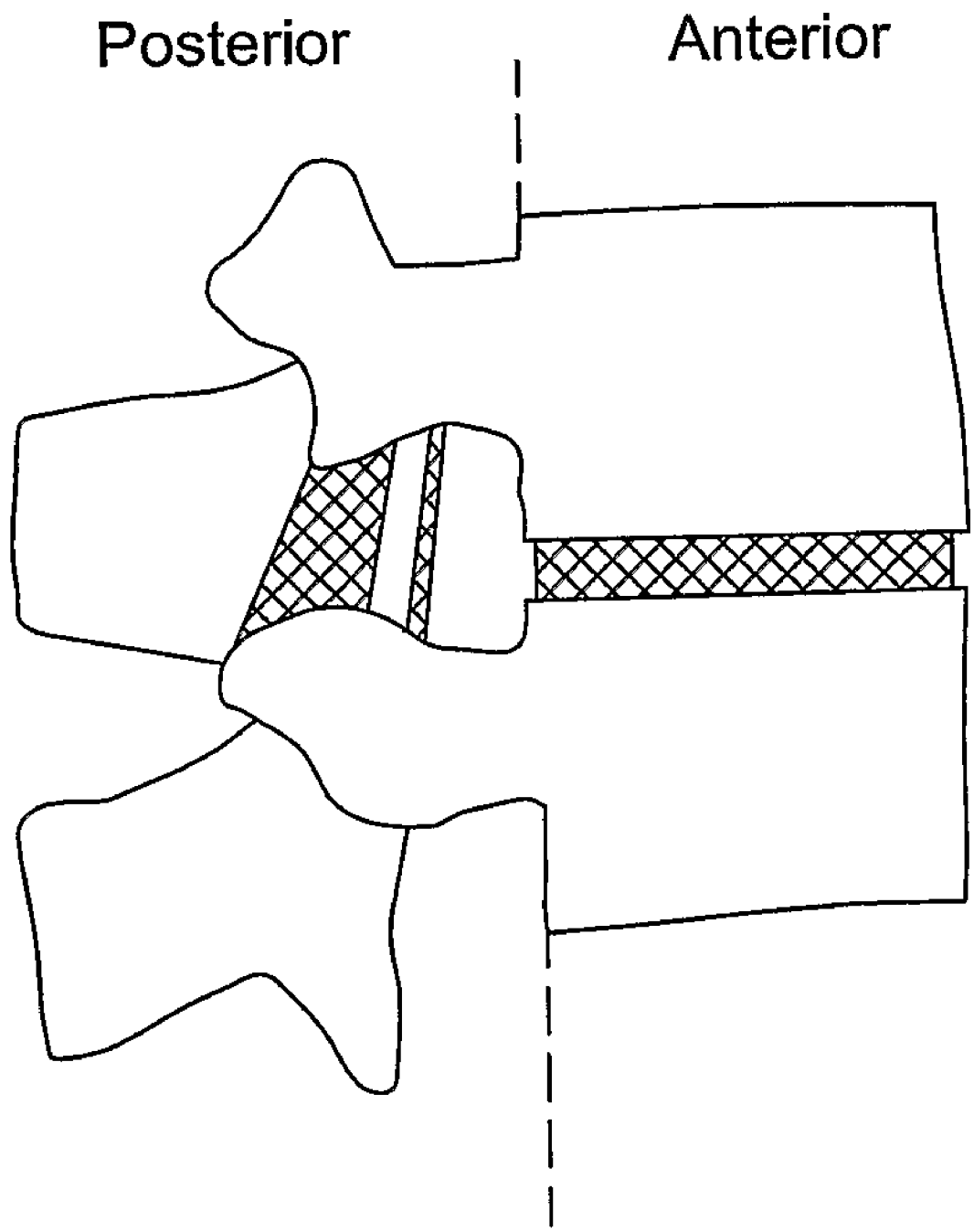
FIG. 1 is a typical motion segment, which includes a pair of adjacent vertebrae separated in the anterior portion by a natural intervertebral disc, and in the posterior portion by the joints of the laminae.
Figure 2A:
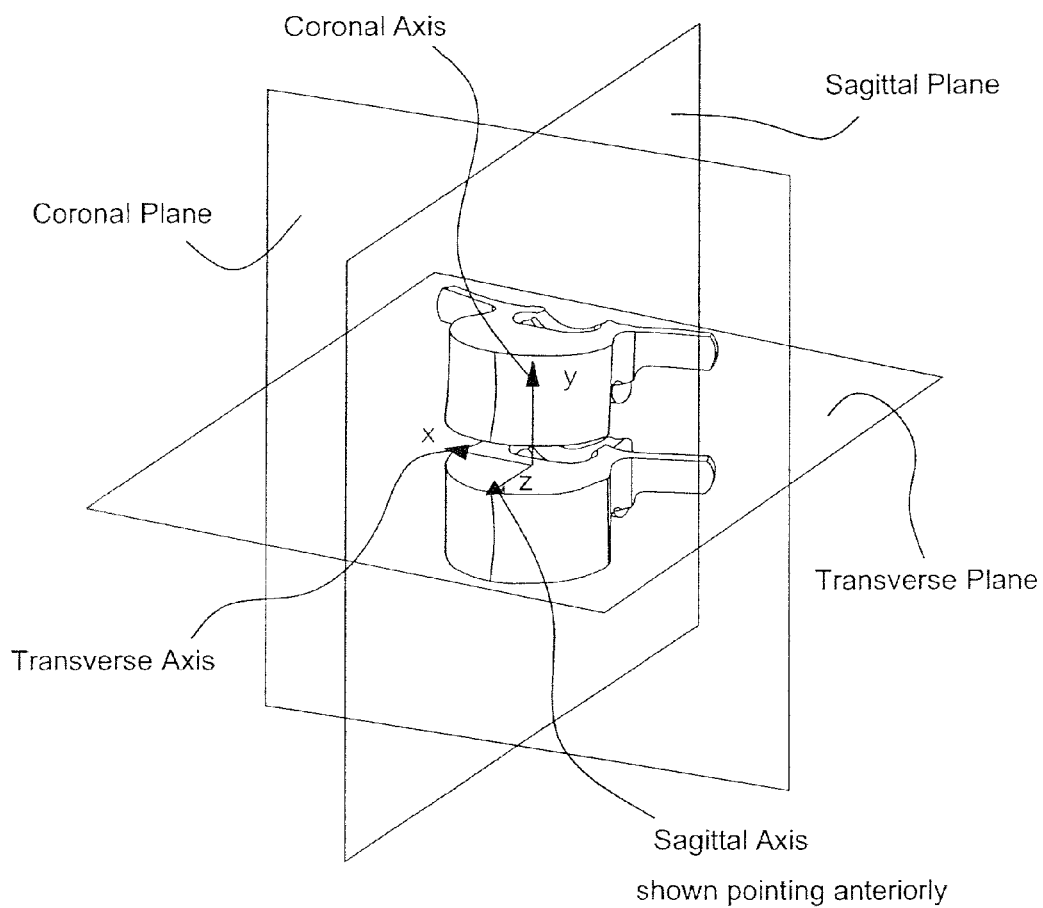
FIG. 2a shows a motion segment and indicates anatomic axes defined relative to the vertebra.
Figure 2B:
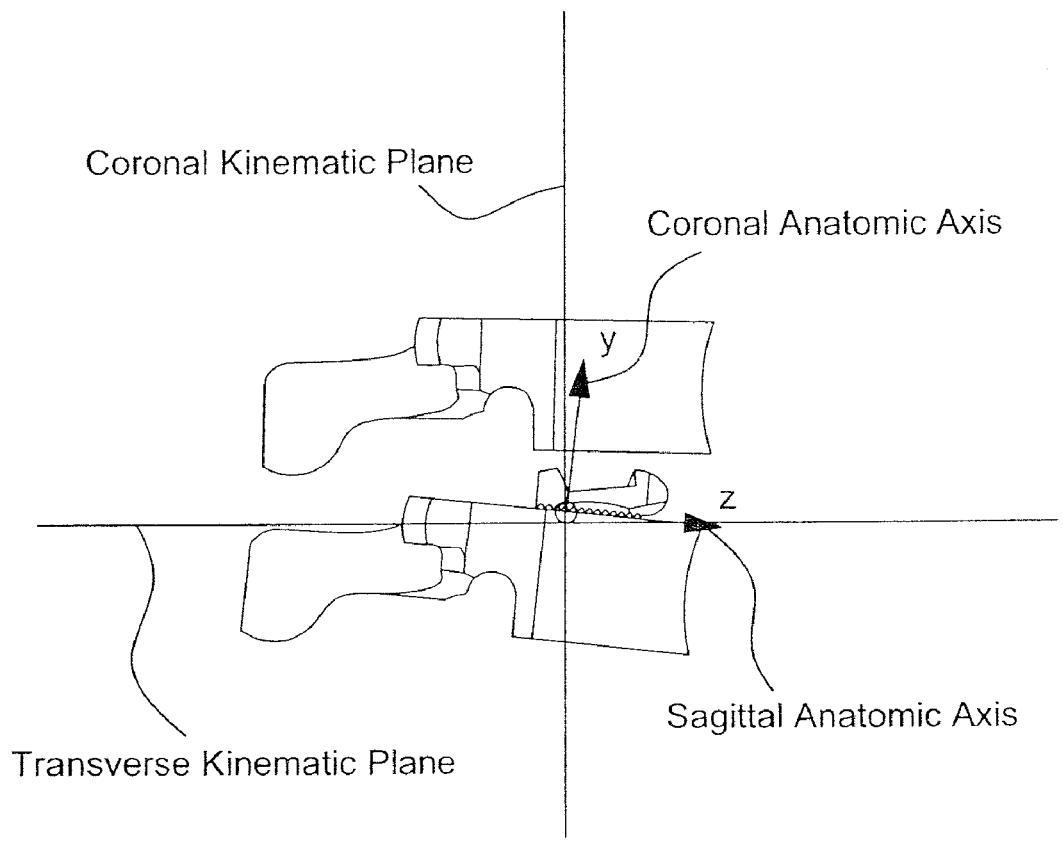
FIG. 2b shows a motion segment and indicates kinematic axes and planes.

Additionally, when in place in the spinal column, a principal axis of the ellipsoidal surface lies in the sagittal plane (defined by the anatomic sagittal axis and the anatomic coronal axis shown in FIG. 2a). However, this principal axis is angled relative to the sagittal axis, preferably so that the anterior portion of the principal axis in the sagittal plane is angled towards the first member. This can be seen with reference to FIG. 3b, in which the portion of the substantially elliptical curve of the first body second member 12 is not symmetric between the posterior and anterior portion or portions of the device.

In this preferred embodiment the vertebra contacting portions 20 and 24 of the second members 12 and 16 respectively are substantially planar. The principal axis of the ellipsoid which can be formed in the bearing surface of the second member to be parallel to the sagittal plane, is made to be angled by 6-8° relative to these substantially planar vertebra contacting portions.

In other words, in the present embodiment, the principal axis of each of the ellipses in the second member bearing surface which can be formed to be parallel to the sagittal plane of the second vertebra 2 when in place in the motion segment, is angled relative to the anatomic transverse plane of the second vertebra. The angle is made so that the principal axis defining the portion of the ellipse in the anterior portion of the second member is tilted towards the first member.

This preferred feature of the invention displaces the portion of the second member bearing surface closest to the first member vertebra contacting portion towards the posterior of the prosthesis. Advantageously, this is towards the line of greatest axial compression along the length of the spine. This promotes a reduction in the shear forces at the bearing interface.

In a preferred embodiment incorporating at least one aspect of the present invention and which is intended for use in the L3/L4 motion segment, the height (i.e. parallel to the coronal axis of the spine) of each of the first and second bodies, when inserted to the motion segment is 14 mm at the anterior of each body, 12 mm at the posterior of each body and each body is 12 mm wide in the lateral direction (i.e. parallel to the transverse axis), and the length of the device is 26 mm from the posterior portion to the anterior portion.

In a preferred embodiment incorporating at least one aspect of the present invention and which is intended for use in the L4/L5 motion segment, the height (i.e. parallel to the coronal axis of the spine) of each of the first and second bodies, when inserted to the motion segment is 14 mm at the anterior of each body, 12 mm at the posterior of each body and each body is 12 mm wide in the lateral direction (i.e. parallel to the transverse axis), and the length of the device is 26 mm from the posterior portion to the anterior portion.

In a preferred embodiment incorporating at least one aspect of the present invention and which is intended for use in the L5/S1 motion segment, the height (i.e. parallel to the coronal axis of the spine) of each of the first and second bodies, when inserted to the motion segment is 15 mm at the anterior of each body, 12 mm at the posterior of each body and each body is 12 mm wide in the lateral direction (i.e. parallel to the transverse axis), and the length of the device is 26 mm from the posterior portion to the anterior portion.

The present invention can provide a range of sizes of prostheses for use in different sized vertebrae, as such the following Table I gives a range of dimension that provide prostheses with the appropriate tapering of the vertebra contacting portions (i.e. the wedge angle) for insertion to the spine:

TABLE I

| Posterior Height | Anterior Height (L4/L5 to L1/L2) | Anterior Height (L5/S1) |
|---|---|---|
| 10 | 12 | 13 |
| 11 | 13 | 14 |
| 12 | 14 | 15 |
| 13 | 15 | 16 |
| 14 | 16 | 17 |
| 15 | 17 | 18 |
| 16 | 18 | 19 |

A range of widths of the prostheses can be envisaged as well, where the width of the prostheses is between 10 mm-18 mm. Similarly, a range of lengths of the prostheses can be envisaged, where the length of the prostheses is between 20 and 30 mm A method of insertion of a bilateral device is also needed, and according to the present invention, includes some of the following steps:

(I) Following surgical incision from the posterior of the patient, the posterior bony ligamentous structures of the motion segment are exposed, and pedicle screws are optionally then inserted into the superior and inferior vertebrae of the appropriate motion segment;

(II) A bilateral facetectomy retaining the midline anatomic structures or a full laminectomy is performed to expose the IVD space;

(III) A partial or full discectomy is then performed;

(IV) The bilateral alignment tool, preferably similar to that discussed above, is positioned such that it is bilaterally symmetric about the sagittal midline using either the spinous processes or in a minimally invasive approach the posterior median spinal furrow as anatomic landmarks. The tool is then inserted into the IVD space such that when fully engaged it bilaterally abuts each respective pars interarticularis, and provides distraction, alignment and neural/soft tissue protection and retraction during the cutting of the prosthesis keel-ways one of, or both, the superior and inferior vertebrae;

(V)The keel-way stop chisel can then be inserted to the guide channel of the bilateral alignment tool and under impaction cut the prosthesis keel-ways until its stop engages the guide, and the bilateral alignment tool can then be removed;

(VI) A body of the prosthesis is then mounted to the insertion instrument;

(VII) Distraction is then provided to the vertebrae, to the contralateral side to which the prosthesis is to be inserted;

(VIII) The prosthesis body is then inserted to the IVD space so that the keel is fully located into the appropriate keel-way;

(IX) If necessary, the other prosthesis body can be similarly inserted to the IVD space;

(X) Compression is applied either between the pedicle screws located in the superior and inferior vertebrae or more preferably the spinous processes of adjacent vertebrae, so that the keels and keel-ways engage to a tight interference fit;

(XI) An impactor may be used to drive the prosthesis forward into the keel-ways.

Figure 20:
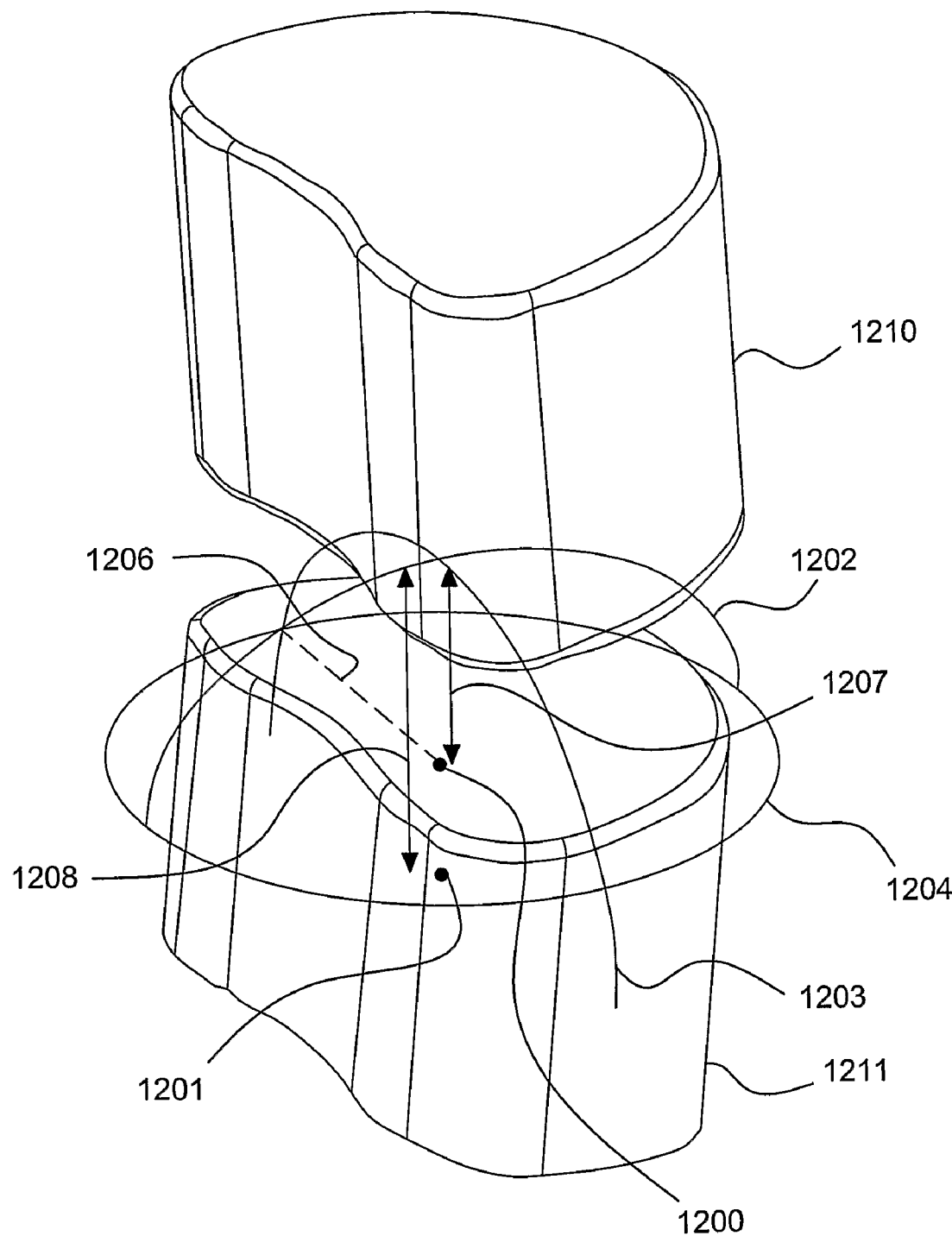
FIG. 20 shows the construction geometry for an embodiment of the present invention.

FIG. 20 shows the construction geometry for an embodiment of the present invention. The two rotation centres 1200, 1201 are used to create three ellipses 1202, 1203 and 1204, which can then be used to create a surface which can be used in the design of a prosthesis according to the present invention. The construction is shown relative to two idealised vertebrae 1210, 1211. The sagittal plane ellipse 1202 and the transverse plane ellipse or circle 1204 are constructed relative to a common centre 1200. However, the coronal plane ellipse 1203 is constructed relative to a different, lower, centre 1201.

In this example, the particular data used is as follows:

TABLE II

| Implant Level | Lordotic Bearing Surface Tilt (°) | Flexion/Extension Ellipse (1202) | | Lateral Flexion Ellipse (1203) | | Torsional Circle (1204) |
|---|---|---|---|---|---|---|
| | | Maj (mm) 1206 | Min (mm) 1207 | Maj (mm) | Min (mm) 1208 | Radius (mm) 1206 |
| L3/L4 | 6 | 27.5 | 14.5 | 29.4 | 22.5 | 27.5 |
| L4/L5 | 6 | 27.5 | 14.5 | 29.4 | 22.5 | 27.5 |
| L5/S1 | 8 | 27.5 | 14.5 | 29.4 | 22.5 | 27.5 |
| Range | 0-15 | 20-35 | 10-25 | 20-40 | 15-30 | 20-35 |

(1200)=fixed flexion/extension rotation centre located approximately 10 mm from posterior aspect of the inferior vertebra and approximately 2 mm below the superior end plate of that vertebra (Ref Pearcy & Bogduk 1988).

(1201)=fixed lateral flexion rotation centre located approximately 10 mm from posterior aspect of the inferior vertebra and approximately 10 mm below the superior end plate of that vertebra (Ref: Zhao et al. 2005).

(1206)=approximate distance from flexion/extension rotation centre (1200) to interfacet midpoint: ~½×mean lateral dimension of a lumbar vertebra (Ref: Berry at al 1987).

(1207) =approximate distance from flexion/extension rotation centre (1200) to mean height of a normal lumbar IVD (Refs: Gilad et al, 1986; Pearcy and Bogduk, 1988).

(1208)=approximate distance from lateral flexion rotation centre (1201) to mean height of a normal lumbar IVD (Refs: Gilad et al, 1986; Zhao et al, 2005).

Advantageously, the elliptical curvature of the present invention can be readily approximated to radial arcs. For example, viewed parallel to the sagittal plane, the elliptical curvature of the bearing surface of the prosthesis can be accurately approximated by a radial arc of the range 35-55 mm, preferably 46 mm. This accuracy is estimated to be within a 0.05 mm (0.002") maximum deviation of the true elliptical curvature of the device in this plane. Notably, the device could be manufactured using this approximation, simplifying production and creating a conforming bearing articulation. Reduced contact stress and hence wear rate could be realised with this configuration compared to a partially or non conforming articulation.

Additionally, for example, viewed parallel to the coronal plane, the elliptical curvature of the bearing surface can be accurately approximated by a radial arc of the range 20-40 mm) preferably 28.9 mm. This accuracy is estimated to be within a 0.05 mm (0.002") maximum deviation of the true elliptical curvature of the device in this plane. The device could be manufactured using this approximation simplifying production and creating conforming bearing articulation.

Reduced contact stress and hence wear rate could be realised with this configuration compared to a partially or non conforming articulation.

When using this geometry to construct a prosthesis, it is preferable that the elliptical portions used are approximated to circular arcs in order to make manufacture of the three-dimensional shape easier.

Figure 21A:
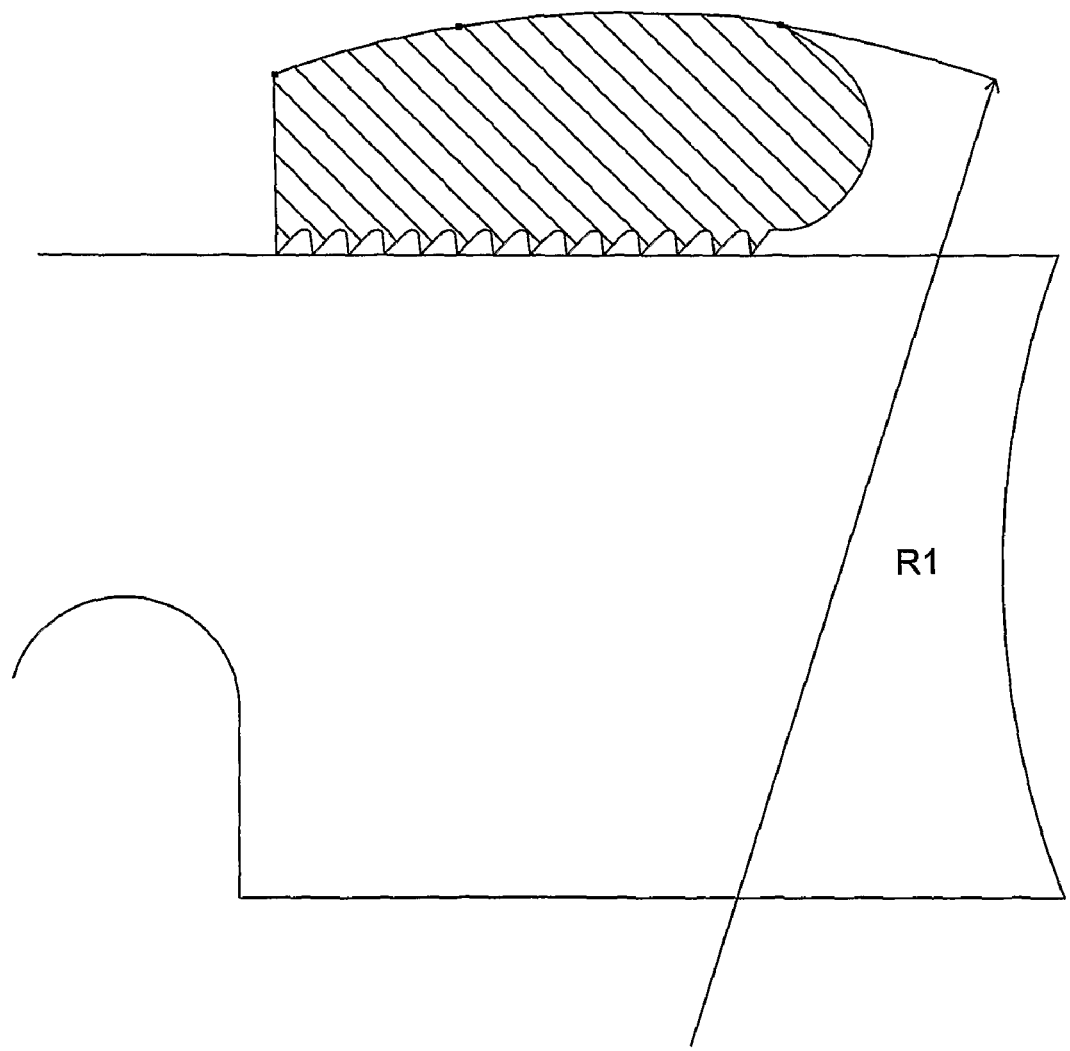
FIG. 21a shows a section of an embodiment of the present invention taken parallel to the sagittal plane, i.e. a medial-lateral view.

FIGS. 21*a*, *b* and *c* show a preferred embodiment in which the radial arc approximations are indicated.

FIG. 21*a* shows a section of an embodiment of the present invention taken parallel to the sagittal plane, i.e. a medial-lateral view. As shown in FIG. 21*a*, R1 is the radial arc approximation of the circular curve in the first body second member bearing surface viewed parallel to the sagittal plane.

Figure 21B:
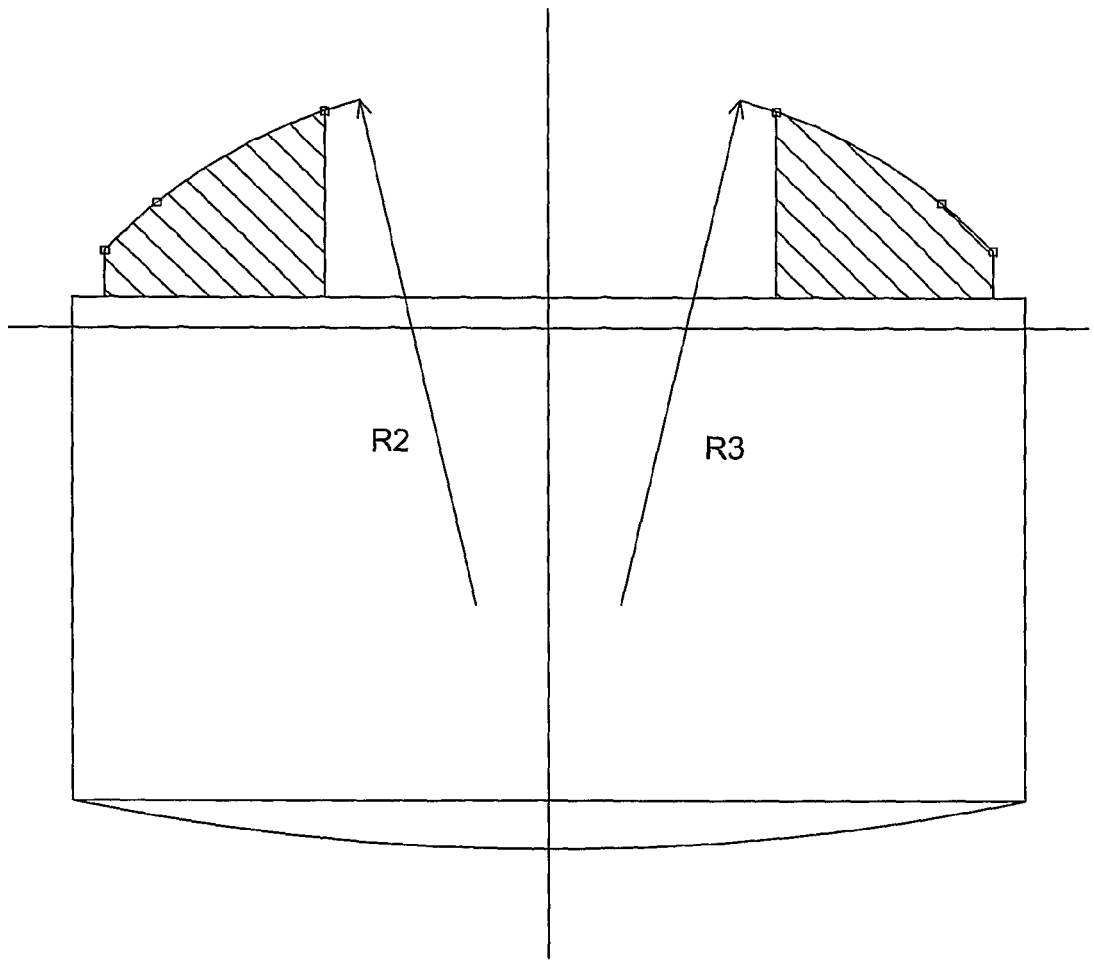
FIG. 21b shows a section of an embodiment of the present invention taken parallel to the coronal plane, i.e. a anterior-posterior view.
Figure 21C:
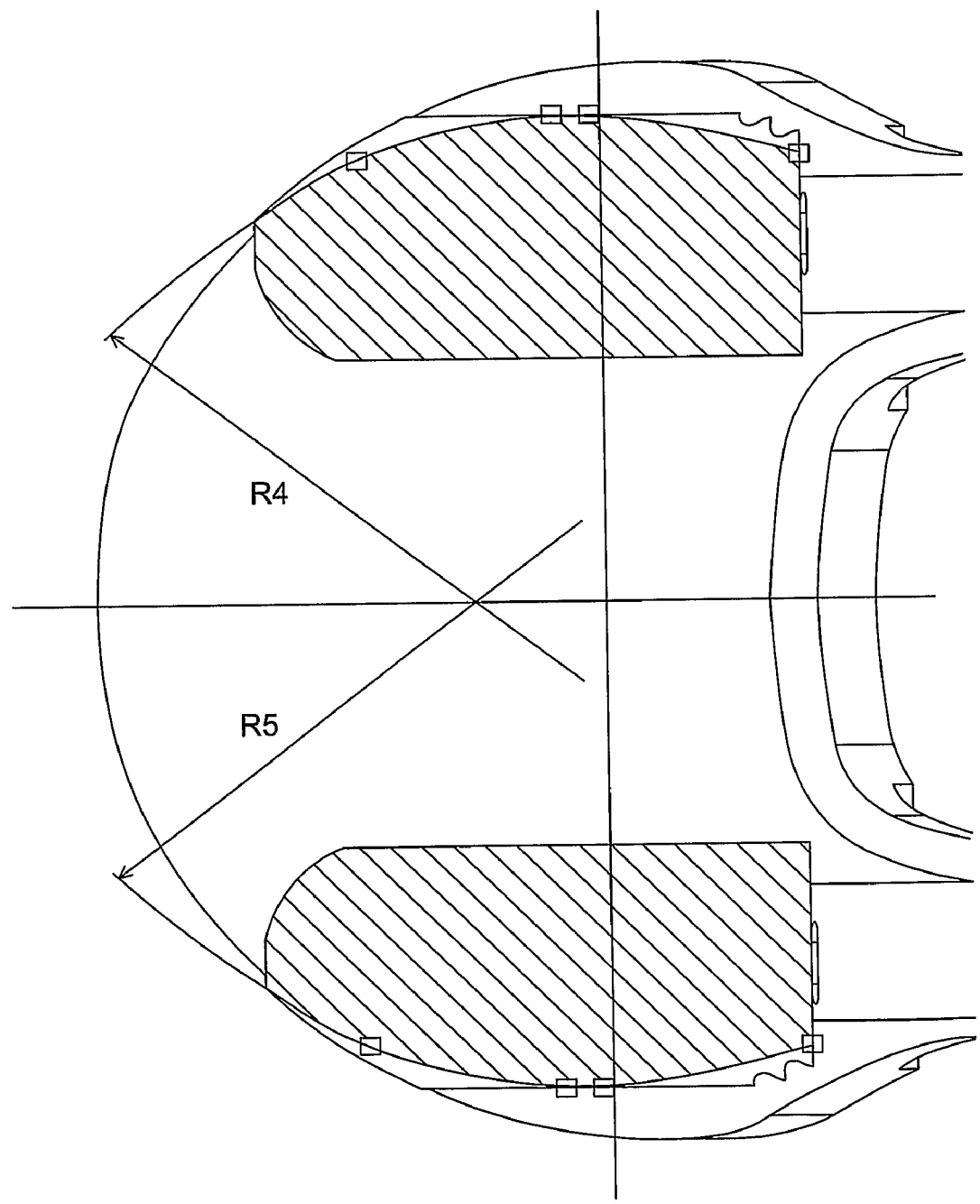
FIG. 21c shows a section of an embodiment of the present invention taken parallel to the transverse plane, i.e. an axial view.

FIGS. 21*b* and *c* show the non-coincidence of the centres of the respectively different circles, of which the second bearing surface is formed in the respective first and second bodies in the different planes.

R2 is the radius of the circular curve in the first body second member bearing surface viewed parallel to the coronal plane, whilst R3 is the radius of the circular curve in the second body second member bearing surface viewed parallel to the coronal plane.

R4 is the radius of the circular curve in the first body second member bearing surface viewed parallel to the transverse plane, whilst R5 is the radius of the circular curve in the second body second member bearing surface viewed parallel to the transverse plane.

The invention claimed is:

1. An articulating intervertebral disc prosthesis including:
    a first member having a vertebra engaging portion, which engages in use a first vertebra, and a bearing surface;
    a second member having a vertebra engaging portion, which engages in use a second vertebra, and a bearing surface, which abuts the first member bearing surface to form a first articulating bearing joint; and
    first and second motion restraint elements adapted to provide articulation restraint of the first articulating bearing joint at pre-determined limits of articulation, thereby defining the limits of the entire range of articulation of the first articulating bearing joint;
    wherein the first and second elements are part of the first and second members respectively; and
    wherein the first and second elements abut each other throughout the entire range of articulation of the first articulating bearing joint to thereby form a second articulating bearing joint which bears throughout the entire range of articulation of the first articulating bearing joint.

2. An articulating intervertebral disc prosthesis according to claim 1, wherein the prosthesis is split into two bodies each having a portion of the first and second articulating bearing joints formed from respective portions of the first and second members, and wherein in use the two bodies are laterally spaced apart.

3. An articulating intervertebral disc prosthesis according to claim 1, wherein the first and second motion restraint elements limit sagittal translation of the first member relative to the second member to 4 mm or less.

4. An articulating intervertebral disc prosthesis according to claim 1, wherein in use, the first and second motion restraint elements limit lateral translation of the first vertebra relative to the second vertebra to 3 mm or less.

5. An articulating intervertebral disc prosthesis according to claim 1, wherein in use the first and second motion restraint elements limit the maximum extent of flexion of the first vertebra relative to the second vertebra to 15° or less.

6. An articulating intervertebral disc prosthesis according to claim 1, wherein in use the first and second motion restraint elements limit the maximum extent of lateral rotation of the first vertebra relative to the second vertebra to 6° or less from the coronal axis.

7. An articulating intervertebral disc prosthesis according to claim 1, wherein in use the first and second motion restraint elements limit the torsional rotation of the first vertebra relative to the second vertebra to a maximum extent of rotation of 5° or less.

8. An articulating intervertebral disc prosthesis according to claim 1, wherein the first motion restraint element includes a finger projecting from the first member bearing surface, wherein the second motion restraint element includes a recess formed in the second member bearing surface for receiving the finger, the recess being defined by sidewalls and a floor, the sidewalls of the recess defining the entire limits of the range of articulation of the first articulating bearing joint by restraining the relative movement of said finger.

9. An articulating intervertebral disc prosthesis according to claim 8, wherein at least a portion of the floor of the recess is engaged by at least a portion of an end face of the projecting finger, the end face of the finger and the recess floor thereby respectively acting to form said second articulating bearing joint.

10. An articulating intervertebral disc prosthesis according to claim 8, wherein said finger includes a first face abuttable against a portion of a first sidewall partially defining said recess, said first face abutting said first sidewall portion at a predetermined limit of extension to form a third articulating bearing joint.

11. An articulating intervertebral disc prosthesis according to claim 10, wherein the first sidewall portion, when viewed in use, in a section parallel to a transverse plane relative to a human body, is at a predetermined constant angle to a transverse axis, such that the third bearing joint permits articulation, within predetermined limits, of the first and second articulating bearing joints in combined lateral rotation and torsion.

12. An articulating intervertebral disc prosthesis according to claim 11, wherein the prosthesis is split into two bodies each having a portion of the first, second and third articulating bearing joints formed from respective portions of the first and second members and wherein in use the two bodies are laterally spaced apart.

13. An articulating intervertebral disc prosthesis according to claim 1, wherein the second member bearing surface of each first and second articulating bearing joint is shaped to include:
    at least a portion of a first circular curve when viewed in use in a first section parallel to a sagittal plane,
    at least a portion of a second circular curve when viewed in use in a second section parallel to a coronal plane, and
    at least a portion of a third circular curve when viewed in use in a third section parallel to a transverse plane, said first, second and third curves being of respectively different sizes of circle such that the second member bearing surface is aspherical.

14. An articulating intervertebral disc prosthesis according to claim 13, wherein the prosthesis is split into two bodies each having a portion of the first and second bearing joints formed from respective portions of the first and second members and wherein in use the two bodies are laterally spaced apart.

15. An articulating intervertebral disc prosthesis according to claim 14, wherein in use the respective articulating bearing joints of the two bodies, articulate about more than one common axis of articulation.

16. An articulating intervertebral disc prosthesis according to claim 14, wherein in use the respective articulating bearing joints of the two bodies cooperate to provide a locus of motion which approximates to a portion of a first ellipse when viewed in the sagittal plane, and a portion of a second ellipse when viewed in the coronal plane, said first and second ellipses being of respectively different sizes.

17. An articulating intervertebral disc prosthesis according to claim 14, wherein in use the respective articulating bearing joints of the two bodies cooperate to maintain substantial conformance throughout the range of articulation in any combination of flexion/extension, lateral and torsional rotation.

18. An articulating intervertebral disc prosthesis according to claim 14, wherein in use the two bodies are laterally spaced apart to provide in use mirror images of one another about the sagittal plane.

19. An articulating intervertebral disc prosthesis according to claim 13, wherein the radius of curvature of the first circular curve is greater than the respective radii of curvature of the second and third curves.

20. An articulating intervertebral disc prosthesis according to claim 13, wherein the radius of curvature of the second circular curve is less than the radius of curvature of the first circular curve but is greater than the radius of curvature of the third circular curve.

21. An articulating intervertebral disc prosthesis according to claim 13, wherein the centre of the circle of which said first circular curve is at least a portion lies in use caudal with respect to the second vertebra.

22. An articulating intervertebral disc prosthesis including:
a first member having a vertebra engaging portion, which in use engages a first vertebra, and a bearing surface; and
a second member having a vertebra engaging portion, which in use engages a second vertebra, and a bearing surface, which in use abuts the first member bearing surface to form an articulating first bearing joint;
wherein the second member bearing surface of the first articulating bearing joint is shaped to include:
at least a portion of a first circular curve when viewed in use in a first section parallel to a sagittal plane,
at least a portion of a second circular curve when viewed in use in a second section parallel to a coronal plane, and
at least a portion of a third circular curve when viewed in use in a third section parallel to a transverse plane, said first, second and third curves being of respectively different sizes of circle such that the second member bearing surface is aspherical; and
wherein the radius of curvature of the first circular curve is greater than the respective radii of curvature of the second and third curves.

23. An articulating intervertebral disc prosthesis according to claim 22, wherein the prosthesis is split into two bodies each having a portion of the first articulating bearing joint formed from respective portions of the first and second members and wherein in use the two bodies are laterally spaced apart.

24. An articulating intervertebral disc prosthesis including:
a first member having a vertebra engaging portion, which in use engages a first vertebra, and a bearing surface; and
a second member having a vertebra engaging portion, which in use engages a second vertebra, and a bearing surface, which in use abuts the first member bearing surface to form a first articulating bearing joint; and
motion restraint means adapted to provide articulation restraint of the first bearing joint at pre-determined limits of articulation;
wherein the motion restraint means includes a recess formed in the second member bearing surface for receiving a finger projecting from the first member bearing surface, the sidewalls of the recess defining the limits of articulation of the first articulating bearing joint by restraining the relative movement of said finger, said finger including a first face abuttable against a portion of a first sidewall partially defining said recess, and said first face abutting said first sidewall portion at a predetermined limit of extension to form a second articulating bearing joint;
wherein the first sidewall portion, when viewed in use, in a section parallel to a transverse plane relative to a human body, is at a predetermined constant angle to a transverse axis, such that the second bearing joint permits articulation, within predetermined limits, of the first articulating bearing joint in combined lateral rotation and torsion.

25. An articulating intervertebral disc prosthesis according to claim 24, wherein the prosthesis is split into two bodies each having a portion of the first and second articulating bearing joints formed from respective portions of the first and second members and wherein in use the two bodies are laterally spaced apart.

* * * * *